(12) United States Patent
Wirbisky et al.

(10) Patent No.: US 9,381,076 B2
(45) Date of Patent: Jul. 5, 2016

(54) SURGICAL ARTICLES AND METHODS

(75) Inventors: Alan G. Wirbisky, Eden Prairie, MN (US); Andrew P. VanDeWeghe, St. Louis Park, MN (US); Randall C. Lieser, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 127 days.

(21) Appl. No.: 13/579,811

(22) PCT Filed: Feb. 23, 2011

(86) PCT No.: PCT/US2011/025917
§ 371 (c)(1),
(2), (4) Date: Aug. 17, 2012

(87) PCT Pub. No.: WO2011/106419
PCT Pub. Date: Sep. 1, 2011

(65) Prior Publication Data
US 2012/0316386 A1 Dec. 13, 2012

Related U.S. Application Data

(60) Provisional application No. 61/307,264, filed on Feb. 23, 2010.

(51) Int. Cl.
*A61F 2/00* (2006.01)
*A61B 17/04* (2006.01)
(Continued)

(52) U.S. Cl.
CPC ........... *A61F 2/0045* (2013.01); *A61B 17/0401* (2013.01); *A61B 17/06109* (2013.01);
(Continued)

(58) Field of Classification Search
CPC ................. A61B 17/0401; A61B 2017/00805; A61B 2017/0409; A61B 2017/0427; A61B 2017/0445; A61B 2017/00349; A61B 2017/0462; A61B 2017/0496; A61B 2017/0408; A61B 2017/0448; A61B 2017/0446; A61B 2017/0464; A61B 2017/0472; A61B 2017/06076; A61B 2017/2837; A61B 17/06109; A61F 2/0045; A61F 2/0004; A61F 2/0031; A61F 2/0036; A61F 2/0063; A61F 2002/0072
USPC .................... 600/29–31, 37; 606/139, 151
See application file for complete search history.

(56) References Cited

U.S. PATENT DOCUMENTS 2,738,790 A 3/1956 Todt, Sr., et al.
3,472,232 A 10/1969 Earl
(Continued)

FOREIGN PATENT DOCUMENTS

AU 2002241673 B2 8/2005
CA 2404459 C 8/2005
(Continued)

OTHER PUBLICATIONS

Non-Final Office Action for U.S. Appl. No. 13/328,488, mailed Jan. 21, 2016, 19 pages.
(Continued)

*Primary Examiner* — Charles A Marmor, II
*Assistant Examiner* — Carrie R Dorna

(57) ABSTRACT

Described are devices, implants, kits, and related methods for treating pelvic conditions such as urinary in incontinence, in a male or a female patient. The invention includes, in one embodiment, a multi-piece implant, including a tissue support piece, extension portion, and one or more self-fixating tips. The device may be employed through a medial incision in the pelvic region of the patient.

18 Claims, 24 Drawing Sheets

(51) Int. Cl.
*A61B 17/06* (2006.01)
*A61B 17/00* (2006.01)
*A61B 17/28* (2006.01)

(52) U.S. Cl.
CPC ............... *A61B2017/00805* (2013.01); *A61B 2017/0408* (2013.01); *A61B 2017/0409* (2013.01); *A61B 2017/0446* (2013.01); *A61B 2017/0448* (2013.01); *A61B 2017/0464* (2013.01); *A61B 2017/0472* (2013.01); *A61B 2017/0496* (2013.01); *A61B 2017/06076* (2013.01); *A61B 2017/2837* (2013.01)

(56) References Cited

U.S. PATENT DOCUMENTS

| | | |
|---|---|---|
| 3,580,313 A | 5/1971 | McKnight |
| 3,763,860 A | 10/1973 | Clarke |
| 3,858,783 A | 1/1975 | Kapitanov et al. |
| 3,995,619 A | 12/1976 | Glatzer |
| 4,172,458 A | 10/1979 | Pereyra |
| 4,235,238 A | 11/1980 | Ogiu et al. |
| 4,441,497 A | 4/1984 | Paudler |
| 4,509,516 A | 4/1985 | Richmond |
| 4,548,202 A | 10/1985 | Duncan |
| 4,632,100 A | 12/1986 | Somers et al. |
| 4,873,976 A | 10/1989 | Schreiber |
| 4,932,962 A | 6/1990 | Yoon et al. |
| 4,938,760 A | 7/1990 | Burton et al. |
| 4,969,892 A | 11/1990 | Burton et al. |
| 4,979,956 A | 12/1990 | Silvestrini |
| 5,013,292 A | 5/1991 | Lemay |
| 5,013,316 A | 5/1991 | Goble et al. |
| 5,053,043 A | 10/1991 | Gottesman et al. |
| 5,085,661 A | 2/1992 | Moss |
| 5,112,344 A | 5/1992 | Petros |
| 5,141,520 A | 8/1992 | Goble et al. |
| 5,149,329 A | 9/1992 | Richardson |
| 5,188,636 A | 2/1993 | Fedotov |
| 5,203,864 A | 4/1993 | Phillips |
| 5,209,756 A | 5/1993 | Seedhom et al. |
| 5,234,438 A | 8/1993 | Semrad |
| 5,256,133 A | 10/1993 | Spitz |
| 5,268,001 A | 12/1993 | Nicholson et al. |
| 5,269,783 A | 12/1993 | Sander |
| 5,281,237 A | 1/1994 | Gimpelson |
| 5,328,077 A | 7/1994 | Lou |
| 5,337,736 A | 8/1994 | Reddy |
| 5,354,292 A | 10/1994 | Braeuer et al. |
| 5,368,595 A | 11/1994 | Lewis |
| 5,370,650 A | 12/1994 | Tovey et al. |
| 5,370,662 A | 12/1994 | Stone et al. |
| 5,376,097 A | 12/1994 | Phillips |
| 5,383,904 A | 1/1995 | Totakura et al. |
| 5,403,328 A | 4/1995 | Shallman |
| 5,439,467 A | 8/1995 | Benderev et al. |
| 5,474,518 A | 12/1995 | Farrer Velazquez |
| 5,474,543 A | 12/1995 | McKay |
| 5,520,700 A | 5/1996 | Beyar et al. |
| 5,520,703 A | 5/1996 | Essig et al. |
| 5,527,342 A | 6/1996 | Pietrzak et al. |
| 5,544,664 A | 8/1996 | Benderev et al. |
| 5,562,689 A | 10/1996 | Green et al. |
| 5,571,139 A | 11/1996 | Jenkins, Jr. |
| 5,582,188 A | 12/1996 | Benderev et al. |
| 5,584,860 A | 12/1996 | Goble et al. |
| 5,591,163 A | 1/1997 | Thompson |
| 5,591,206 A | 1/1997 | Moufarrege |
| 5,611,515 A | 3/1997 | Benderev et al. |
| 5,628,756 A | 5/1997 | Barker, Jr. et al. |
| 5,643,320 A | 7/1997 | Lower et al. |
| 5,647,836 A | 7/1997 | Blake, III et al. |
| 5,669,935 A | 9/1997 | Rosenman et al. |
| 5,674,247 A | 10/1997 | Sohn |
| 5,683,349 A | 11/1997 | Makower et al. |
| 5,690,655 A | 11/1997 | Hart et al. |
| 5,697,931 A | 12/1997 | Thompson |
| 5,709,708 A | 1/1998 | Thal |
| 5,725,529 A | 3/1998 | Nicholson et al. |
| 5,725,541 A | 3/1998 | Anspach, III et al. |
| 5,741,282 A | 4/1998 | Anspach, III et al. |
| 5,782,862 A | 7/1998 | Bonutti |
| 5,842,478 A | 12/1998 | Benderev et al. |
| 5,860,425 A | 1/1999 | Benderev et al. |
| 5,873,891 A | 2/1999 | Sohn |
| 5,899,909 A | 5/1999 | Claren et al. |
| 5,904,692 A | 5/1999 | Steckel et al. |
| 5,922,026 A | 7/1999 | Chin |
| 5,925,047 A | 7/1999 | Errico et al. |
| 5,944,732 A | 8/1999 | Raulerson et al. |
| 5,954,057 A | 9/1999 | Li |
| 5,972,000 A | 10/1999 | Beyar et al. |
| 5,980,558 A | 11/1999 | Wiley |
| 5,984,927 A | 11/1999 | Wenstrom, Jr., et al. |
| 5,988,171 A | 11/1999 | Sohn et al. |
| 5,997,554 A | 12/1999 | Thompson |
| 6,007,539 A | 12/1999 | Kirsch et al. |
| 6,019,768 A | 2/2000 | Wenstrom, Jr., et al. |
| 6,027,523 A | 2/2000 | Schmieding |
| 6,030,393 A | 2/2000 | Corlew |
| 6,036,701 A | 3/2000 | Rosenman |
| 6,039,686 A | 3/2000 | Kovac |
| 6,042,534 A | 3/2000 | Gellman et al. |
| 6,042,583 A | 3/2000 | Thompson et al. |
| 6,048,351 A | 4/2000 | Gordon et al. |
| 6,053,935 A | 4/2000 | Brenneman et al. |
| 6,056,688 A | 5/2000 | Benderev et al. |
| 6,099,538 A | 8/2000 | Moses et al. |
| 6,099,551 A | 8/2000 | Gabbay |
| 6,099,552 A | 8/2000 | Adams |
| 6,110,101 A | 8/2000 | Tihon et al. |
| 6,127,597 A | 10/2000 | Beyar et al. |
| 6,168,611 B1 | 1/2001 | Rizvi |
| 6,200,330 B1 | 3/2001 | Benderev et al. |
| 6,241,736 B1 | 6/2001 | Sater et al. |
| 6,245,082 B1 | 6/2001 | Gellman et al. |
| 6,264,676 B1 | 7/2001 | Gellman et al. |
| 6,273,852 B1 | 8/2001 | Lehe et al. |
| 6,319,272 B1 | 11/2001 | Brenneman et al. |
| 6,322,492 B1 | 11/2001 | Kovac |
| 6,328,744 B1 | 12/2001 | Harari et al. |
| 6,334,446 B1 | 1/2002 | Beyar |
| 6,382,214 B1 | 5/2002 | Raz et al. |
| 6,387,041 B1 | 5/2002 | Harari et al. |
| 6,406,423 B1 | 6/2002 | Scetbon |
| 6,406,480 B1 | 6/2002 | Beyar et al. |
| 6,409,733 B1 | 6/2002 | Conlon et al. |
| 6,423,072 B1 | 7/2002 | Zappala |
| 6,423,080 B1 | 7/2002 | Gellman et al. |
| 6,440,154 B2 | 8/2002 | Gellman et al. |
| 6,451,024 B1 | 9/2002 | Thompson et al. |
| 6,454,778 B2 | 9/2002 | Kortenbach |
| 6,475,139 B1 | 11/2002 | Miller |
| 6,478,727 B2 | 11/2002 | Seetbon |
| 6,491,703 B1 | 12/2002 | Ulmsten |
| 6,502,578 B2 | 1/2003 | Raz et al. |
| 6,506,190 B1 | 1/2003 | Walshe |
| 6,530,943 B1 | 3/2003 | Hoepffner et al. |
| 6,544,273 B1 | 4/2003 | Harari et al. |
| 6,582,443 B2 | 6/2003 | Cabak et al. |
| 6,592,515 B2 | 7/2003 | Thierfelder et al. |
| 6,592,610 B2 | 7/2003 | Beyar |
| 6,596,001 B2 | 7/2003 | Stormby et al. |
| 6,599,235 B2 | 7/2003 | Kovac |
| 6,602,260 B2 | 8/2003 | Harari et al. |
| 6,612,977 B2 | 9/2003 | Staskin et al. |
| 6,635,058 B2 | 10/2003 | Beyar et al. |
| 6,638,210 B2 | 10/2003 | Berger |
| 6,638,211 B2 | 10/2003 | Suslian et al. |
| 6,641,525 B2 | 11/2003 | Rocheleau et al. |
| 6,673,010 B2 | 1/2004 | Skiba et al. |
| 6,685,629 B2 | 2/2004 | Therin |
| 6,689,047 B2 | 2/2004 | Gellman |
| 6,730,110 B1 | 5/2004 | Harari et al. |

(56) References Cited

U.S. PATENT DOCUMENTS

| | | |
|---|---|---|
| 6,746,455 B2 | 6/2004 | Beyar et al. |
| 6,752,814 B2 | 6/2004 | Gellman et al. |
| 6,802,807 B2 | 10/2004 | Anderson et al. |
| 6,845,082 B2 | 1/2005 | Bourget et al. |
| 6,884,212 B2 | 4/2005 | Thierfelder et al. |
| 6,908,425 B2 | 6/2005 | Luscombe |
| 6,908,473 B2 | 6/2005 | Skiba et al. |
| 6,911,002 B2 | 6/2005 | Fierro |
| 6,911,003 B2 | 6/2005 | Anderson et al. |
| 6,932,759 B2 | 8/2005 | Kammerer et al. |
| 6,936,052 B2 | 8/2005 | Gellman et al. |
| 6,971,986 B2 | 12/2005 | Staskin et al. |
| 6,974,462 B2 | 12/2005 | Sater |
| 6,981,983 B1 | 1/2006 | Rosenblatt et al. |
| 6,991,597 B2 | 1/2006 | Gellman et al. |
| 7,014,607 B2 | 3/2006 | Gellman |
| 7,025,772 B2 | 4/2006 | Gellman et al. |
| 7,037,255 B2 | 5/2006 | Inman et al. |
| 7,048,682 B2 | 5/2006 | Neisz et al. |
| 7,056,333 B2 | 6/2006 | Walshe |
| 7,070,556 B2 | 7/2006 | Anderson et al. |
| 7,083,637 B1 | 8/2006 | Tannhauser |
| 7,087,059 B2 | 8/2006 | Harari et al. |
| 7,112,171 B2 | 9/2006 | Rocheleau et al. |
| 7,121,997 B2 | 10/2006 | Kammerer et al. |
| 7,131,943 B2 | 11/2006 | Kammerer |
| 7,223,229 B2 | 5/2007 | Inman et al. |
| 7,226,407 B2 | 6/2007 | Kammerer et al. |
| 7,226,408 B2 | 6/2007 | Harai et al. |
| 7,226,409 B2 | 6/2007 | Peng et al. |
| 7,229,404 B2 | 6/2007 | Bouffier |
| 7,229,453 B2 | 6/2007 | Anderson et al. |
| 7,235,043 B2 | 6/2007 | Gellman et al. |
| 7,261,723 B2 | 8/2007 | Smith et al. |
| 7,267,645 B2 | 9/2007 | Anderson et al. |
| 7,291,104 B2 | 11/2007 | Neisz et al. |
| 7,297,102 B2 | 11/2007 | Smith et al. |
| 7,303,525 B2 | 12/2007 | Watschke et al. |
| 7,326,213 B2 | 2/2008 | Benderev et al. |
| 7,347,812 B2 | 3/2008 | Mellier |
| 7,351,196 B2 | 4/2008 | Goldmann et al. |
| 7,351,197 B2 | 4/2008 | Montpetit et al. |
| 7,357,773 B2 | 4/2008 | Watschke |
| 7,364,541 B2 | 4/2008 | Chu et al. |
| 7,371,245 B2 | 5/2008 | Evans et al. |
| 7,387,634 B2 | 6/2008 | Benderev |
| 7,393,320 B2 | 7/2008 | Montpetit et al. |
| 7,407,480 B2 | 8/2008 | Staskin et al. |
| 7,410,460 B2 | 8/2008 | Benderev |
| 7,413,540 B2 | 8/2008 | Gellman et al. |
| 7,422,557 B2 | 9/2008 | Arnal et al. |
| 7,494,495 B2 | 2/2009 | Delorme et al. |
| 7,500,945 B2 | 3/2009 | Cox et al. |
| 7,517,313 B2 | 4/2009 | Thierfelder et al. |
| 7,527,588 B2 | 5/2009 | Zaddem et al. |
| 7,527,633 B2 | 5/2009 | Rioux |
| 7,547,316 B2 | 6/2009 | Priewe et al. |
| 7,588,598 B2 | 9/2009 | Delorme et al. |
| 7,601,118 B2 | 10/2009 | Smith et al. |
| 7,614,999 B2 | 11/2009 | Gellman et al. |
| 7,621,865 B2 | 11/2009 | Gellman et al. |
| 7,637,860 B2 | 12/2009 | MacLean |
| 7,686,759 B2 | 3/2010 | Sater |
| 7,686,760 B2 | 3/2010 | Anderson et al. |
| 7,691,050 B2 | 4/2010 | Gellman et al. |
| 7,691,052 B2 | 4/2010 | Gellman et al. |
| 7,740,576 B2 | 6/2010 | Hodroff et al. |
| 7,753,839 B2 | 7/2010 | Siegel et al. |
| 7,762,942 B2 | 7/2010 | Neisz et al. |
| 7,828,715 B2 | 11/2010 | Haverfield et al. |
| 8,727,963 B2 * | 5/2014 | Knoll ............................ 600/30 |
| 2001/0000533 A1 | 4/2001 | Kovac |
| 2001/0018549 A1 | 8/2001 | Scetbon |
| 2001/0027321 A1 | 10/2001 | Gellman et al. |
| 2001/0041895 A1 | 11/2001 | Beyar et al. |
| 2001/0049467 A1 | 12/2001 | Lehe et al. |
| 2001/0053916 A1 | 12/2001 | Rioux |
| 2002/0007222 A1 | 1/2002 | Desai |
| 2002/0028980 A1 | 3/2002 | Thierfelder et al. |
| 2002/0035369 A1 | 3/2002 | Beyar et al. |
| 2002/0038119 A1 | 3/2002 | Weber et al. |
| 2002/0038132 A1 | 3/2002 | Abrams |
| 2002/0050277 A1 | 5/2002 | Beyar |
| 2002/0055748 A1 | 5/2002 | Gellman et al. |
| 2002/0058959 A1 | 5/2002 | Gellman |
| 2002/0068948 A1 | 6/2002 | Stormby et al. |
| 2002/0077526 A1 | 6/2002 | Kammerer et al. |
| 2002/0082619 A1 | 6/2002 | Cabak et al. |
| 2002/0091373 A1 | 7/2002 | Berger |
| 2002/0095064 A1 | 7/2002 | Beyar |
| 2002/0095163 A1 | 7/2002 | Beyar |
| 2002/0095181 A1 | 7/2002 | Beyar |
| 2002/0107525 A1 | 8/2002 | Harari et al. |
| 2002/0128681 A1 | 9/2002 | Broome et al. |
| 2002/0147382 A1 | 10/2002 | Neisz et al. |
| 2002/0151909 A1 | 10/2002 | Gellman et al. |
| 2002/0156487 A1 | 10/2002 | Gellman et al. |
| 2002/0156488 A1 | 10/2002 | Gellman et al. |
| 2002/0161382 A1 | 10/2002 | Neisz et al. |
| 2002/0188169 A1 | 12/2002 | Kammerer et al. |
| 2003/0004395 A1 | 1/2003 | Therin |
| 2003/0009181 A1 | 1/2003 | Gellman et al. |
| 2003/0023136 A1 | 1/2003 | Raz et al. |
| 2003/0023138 A1 | 1/2003 | Luscombe |
| 2003/0036676 A1 | 2/2003 | Scetbon |
| 2003/0045774 A1 | 3/2003 | Staskin et al. |
| 2003/0050530 A1 | 3/2003 | Neisz et al. |
| 2003/0065402 A1 | 4/2003 | Anderson et al. |
| 2003/0171644 A1 | 9/2003 | Anderson et al. |
| 2003/0176875 A1 | 9/2003 | Anderson et al. |
| 2004/0015057 A1 | 1/2004 | Rocheleau et al. |
| 2004/0039453 A1 | 2/2004 | Anderson et al. |
| 2004/0073235 A1 | 4/2004 | Lund et al. |
| 2004/0106847 A1 * | 6/2004 | Benderev .................... 600/37 |
| 2004/0193215 A1 | 9/2004 | Harari et al. |
| 2004/0225181 A1 | 11/2004 | Chu et al. |
| 2004/0267088 A1 | 12/2004 | Kammerer |
| 2005/0000523 A1 | 1/2005 | Beraud |
| 2005/0004576 A1 | 1/2005 | Benderev |
| 2005/0131391 A1 | 6/2005 | Chu et al. |
| 2005/0131393 A1 | 6/2005 | Chu et al. |
| 2005/0199249 A1 | 9/2005 | Karram |
| 2005/0245787 A1 | 11/2005 | Cox et al. |
| 2005/0256530 A1 | 11/2005 | Petros |
| 2005/0277806 A1 | 12/2005 | Cristalli |
| 2005/0278037 A1 | 12/2005 | Delorme et al. |
| 2005/0283189 A1 | 12/2005 | Rosenblatt |
| 2006/0058578 A1 | 3/2006 | Browning |
| 2006/0089524 A1 | 4/2006 | Chu |
| 2006/0089525 A1 | 4/2006 | Mamo et al. |
| 2006/0161188 A1 | 7/2006 | Kennedy, II |
| 2006/0195007 A1 | 8/2006 | Anderson et al. |
| 2006/0195010 A1 | 8/2006 | Arnal et al. |
| 2006/0195011 A1 | 8/2006 | Arnal et al. |
| 2006/0217589 A1 | 9/2006 | Wan et al. |
| 2006/0229493 A1 | 10/2006 | Weiser et al. |
| 2006/0229596 A1 | 10/2006 | Weiser et al. |
| 2006/0252980 A1 | 11/2006 | Arnal et al. |
| 2006/0260618 A1 | 11/2006 | Hodroff et al. |
| 2006/0287571 A1 | 12/2006 | Gozzi et al. |
| 2007/0015953 A1 | 1/2007 | MacLean |
| 2007/0043255 A1 | 2/2007 | O'Donnell |
| 2007/0078295 A1 | 4/2007 | Landgrebe |
| 2007/0173864 A1 | 7/2007 | Chu |
| 2008/0039678 A1 | 2/2008 | Montpetit et al. |
| 2008/0200751 A1 * | 8/2008 | Browning ..................... 600/30 |
| 2008/0300607 A1 | 12/2008 | Meade et al. |
| 2009/0012353 A1 | 1/2009 | Beyer |
| 2009/0182190 A1 | 7/2009 | Dann |
| 2009/0221867 A1 | 9/2009 | Ogdahl et al. |
| 2009/0221868 A1 | 9/2009 | Evans |
| 2009/0259092 A1 | 10/2009 | Ogdahl et al. |
| 2010/0010631 A1 | 1/2010 | Otte et al. |
| 2010/0094079 A1 | 4/2010 | Inman et al. |

(56) References Cited

U.S. PATENT DOCUMENTS

| | | | |
|---|---|---|---|
| 2010/0256442 A1 | 10/2010 | Ogdahl et al. |
| 2010/0261952 A1 | 10/2010 | Montpetit et al. |
| 2010/0261955 A1 | 10/2010 | O'Hern |
| 2011/0034759 A1 | 2/2011 | Ogdahl et al. |
| 2011/0112357 A1 | 5/2011 | Chapman et al. |

FOREIGN PATENT DOCUMENTS

| | | |
|---|---|---|
| DE | 2305815 A1 | 8/1974 |
| DE | 4220283 C2 | 5/1994 |
| DE | 20016866 U1 | 12/2000 |
| EP | 0632999 A1 | 1/1995 |
| EP | 0643945 A2 | 3/1995 |
| EP | 0650703 A1 | 5/1995 |
| EP | 1342450 B1 | 1/2007 |
| FR | 2852813 A1 | 10/2004 |
| FR | 2852817 A1 | 10/2004 |
| GB | 2268690 A | 1/1994 |
| GB | 2353220 A | 2/2001 |
| SU | 1342486 A1 | 10/1987 |
| WO | 93/10715 A2 | 6/1993 |
| WO | 93/19678 A2 | 10/1993 |
| WO | 95/11631 A1 | 5/1995 |
| WO | 95/25469 A1 | 9/1995 |
| WO | 97/16121 A1 | 5/1997 |
| WO | 97/30638 A1 | 8/1997 |
| WO | 97/47244 A1 | 12/1997 |
| WO | 98/19606 A1 | 5/1998 |
| WO | 98/35606 A2 | 8/1998 |
| WO | 98/35616 A1 | 8/1998 |
| WO | 98/42261 A1 | 10/1998 |
| WO | 98/53746 A1 | 12/1998 |
| WO | 99/37216 A1 | 7/1999 |
| WO | 99/37217 A1 | 7/1999 |
| WO | 99/52450 A1 | 10/1999 |
| WO | 99/53844 A1 | 10/1999 |
| WO | 99/58074 A2 | 11/1999 |
| WO | 99/59477 A1 | 11/1999 |
| WO | 00/13601 A1 | 3/2000 |
| WO | 00/30556 A1 | 6/2000 |
| WO | 00/040158 A2 | 7/2000 |
| WO | 00/057796 A1 | 10/2000 |
| WO | 00/074594 A1 | 12/2000 |
| WO | 00/074613 A1 | 12/2000 |
| WO | 00/074633 A2 | 12/2000 |
| WO | 02/30293 A1 | 4/2002 |
| WO | 02/32284 A2 | 4/2002 |
| WO | 02/34124 A2 | 5/2002 |
| WO | WO 02/39890 | 5/2002 |
| WO | 02/058563 A1 | 8/2002 |
| WO | 02/062237 A1 | 8/2002 |
| WO | 02/071953 A2 | 9/2002 |
| WO | WO 02/069781 | 9/2002 |
| WO | 03/013392 A1 | 2/2003 |
| WO | 03/017848 A1 | 3/2003 |
| WO | 03/034939 A1 | 5/2003 |
| WO | 03/047435 A1 | 6/2003 |
| WO | 03/068107 A1 | 8/2003 |
| WO | 03/075792 A1 | 9/2003 |
| WO | 03/086205 A2 | 10/2003 |
| WO | 03/092546 A2 | 11/2003 |
| WO | 03/096928 A1 | 11/2003 |
| WO | 03/096929 A1 | 11/2003 |
| WO | 2004/016196 A2 | 2/2004 |
| WO | 2004/034912 A1 | 4/2004 |
| WO | 2005/004727 A1 | 1/2005 |
| WO | 2005/046511 A2 | 5/2005 |
| WO | 2005/048850 A2 | 6/2005 |
| WO | 2005/079702 A1 | 9/2005 |
| WO | 2005/122954 A1 | 12/2005 |
| WO | 2006/007189 A1 | 1/2006 |
| WO | 2006/007190 A1 | 1/2006 |
| WO | 2006/031879 A1 | 3/2006 |
| WO | 2006/069078 A2 | 6/2006 |
| WO | 2006/108145 A1 | 10/2006 |
| WO | 2007/002012 A1 | 1/2007 |
| WO | 2007/002071 A1 | 1/2007 |
| WO | 2007/014241 A1 | 2/2007 |
| WO | WO 2007/016083 | 2/2007 |
| WO | 2007/027592 A1 | 3/2007 |
| WO | 2007/059199 A2 | 5/2007 |
| WO | WO 2007/097994 | 8/2007 |
| WO | 2007/137226 A2 | 11/2007 |
| WO | 2007/146784 A2 | 12/2007 |
| WO | WO 2007/149348 | 12/2007 |
| WO | 2008/057261 A2 | 5/2008 |
| WO | 2008/124056 A1 | 10/2008 |
| WO | 2009/005714 A2 | 1/2009 |
| WO | 2009/017680 A2 | 2/2009 |
| WO | WO 2009/075800 | 6/2009 |
| WO | WO 2009/145911 | 12/2009 |
| WO | WO 2010/093421 | 8/2010 |

OTHER PUBLICATIONS

Ulmsten et al., "An Ambulatory Surgical Procedure Under Local Anesthesia For Treatment Of Female Urinary Incontinence", International Urogynecology Journal, vol. 7, May 1996, pp. 81-86.

"We're Staying Ahead of the Curve", Introducing the IVS Tunneller Device for Tension Free Procedures, Tyco Healthcare, 2002, 3 pages.

Advantage AT™, Surgical Mesh Sling Kit, Boston Scientific, 2002, 6 pages.

Capio® CL—Transvaginal Suture Capturing Device—Transvaginal suture fixation to Cooper's Ligament for Sling Procedures, Boston Scientific, Microvasive, 2002, 8 pages.

"Gynecare TVT Tension-Free Support for Incontinence, The tension-free Solution to Female Incontinence", Gynecare Worldwide, 2002, 6 pages.

Ulmsten et al., "A Three Year Follow Up Of Tension Free Vaginal Tape For Surgical Treatment Of Female Stress Urinary Incontinence", British Journal of Obstetrics and Gynaecology, vol. 106, 1999, pp. 345-350.

"Low Profile Design for Precise Anchor Placement", Precision Twist, Boston Scientific Microvasive, 2001, 1 page.

"Sabre™ Bioabsorbable Sling", Generation Now, Mentor, May 2002, 4 pages.

"The Precise Approach to Transvaginal Sling Procedures", Precision Tack, Boston Scientific, 1998, 4 pages.

Sanz et al., "Modification Of Abdominal Sacrocolpopexy Using A Suture Anchor System", The Journal of Reproductive Medicine, vol. 48, No. 7, Jul. 2003, pp. 496-500.

"Vesica Sling Kit", Microvasive Boston Scientific, 1997, 4 pages.

Vesica® Percutaneous Bladder Neck Stabilization Kit—A New Approach to Bladder Neck Suspenison, Microvasive® Boston Scientific Corporation, 1995, 4 pages.

Benderev, Theodore V., "A Modified Percutaneous Outpatient Bladder Neck Suspension System", Journal of Urology, vol. 152, Dec. 1994, pp. 2316-2320.

Benderev, Theodore V., "Anchor Fixation and Other Modifications of Endoscopic Bladder Neck Suspension", Journal of Urology, vol. 40, Nov. 1992, pp. 409-418.

Mitek Brochure, Therapy of Urinary Stess Incontinence in Women Using Mitek Gill Anchors by Valenzio C. Mascio, MD, 1993, 5 pages.

Cook/Ob Gyn®, "Urogynecology", Copyright Cook Urological Inc., 1996, pp. 1-36.

Dargent et al., "Insertion Of A Suburethral Sling Through The Obturator Membrane In The Treatment of Female Urinary Incontinence", Gynecol Obstet Fertil, vol. 30, 2002, pp. 576-582.

IVS Tunneller, "A Universal Instrument for Anterior and Posterior Intra-Vaginal Tape Placement", Tyco Healthcare, Aug. 2002, 4 pages.

Pelosi et al., "Pubic Bone Suburethral Stabilization Sling: Laparoscopic Assessment Of A Transvaginal Operation For The Treatment Of Stress Urinary Incontinence", Journal of Laparoendoscopic & Advaned Surgical Techniques, vol. 9, No. 1, Feb. 1999, pp. 45-50.

Kovac et al., "Pubic Bone Suburethral Stabilization Sling: A Long Term Cure for SUI?", Contemeorary OB/GYN, Feb. 1998, 8 pages.

(56) References Cited

OTHER PUBLICATIONS

IVS Tunneller, ein universelles Instrument fur die Intra Vaginal Schlingenplastik, Tyco Healthcare, 2001, 4 pages.

Karram et al., "Chapter 19: Surgical Treatment Of Vaginal Vault Prolapse", Urogynecology and Reconstructive Pelvic Surgery, 1999, pp. 235-256.

* cited by examiner

3. PULL OUT GUIDE TUBES.

2. USE GUIDE TUBES TO RE-ENGAGE ANCHOR UNTIL SLING IS CORRECTLY POSITIONED

1. USE INSERTION TOOL TO POSITION ANCHOR.

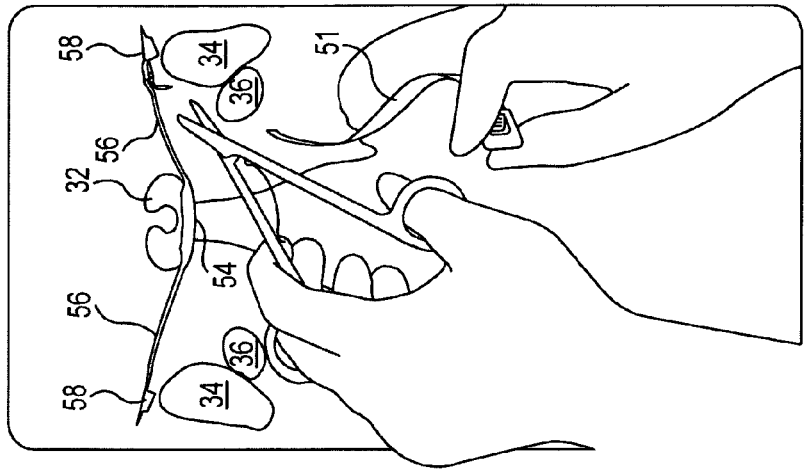
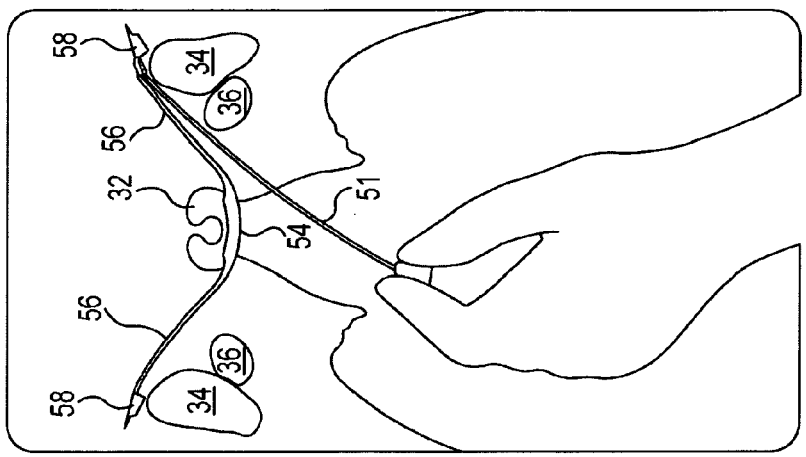
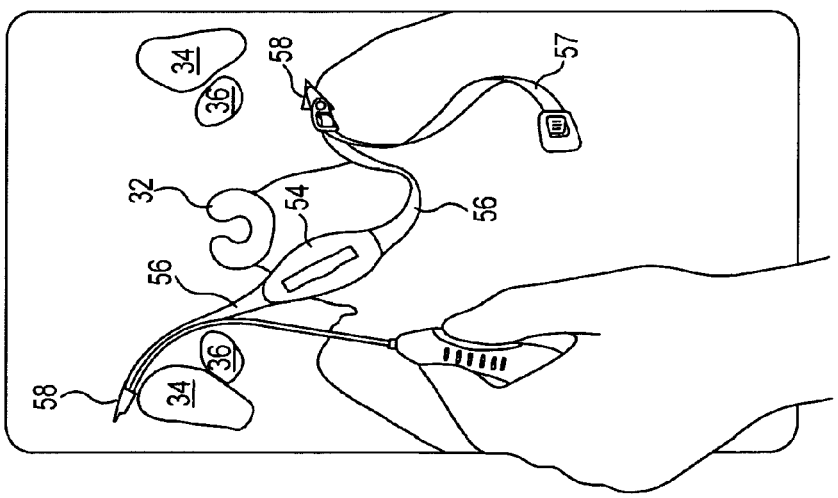

3. TRIM EXCESS MATERIAL.

2. POSITION SLING OVER URETHRA AND SLIDE CLEAT TO SECURE IN POSITION.

1. USE INSERTION TOOL TO POSITION ANCHORS.

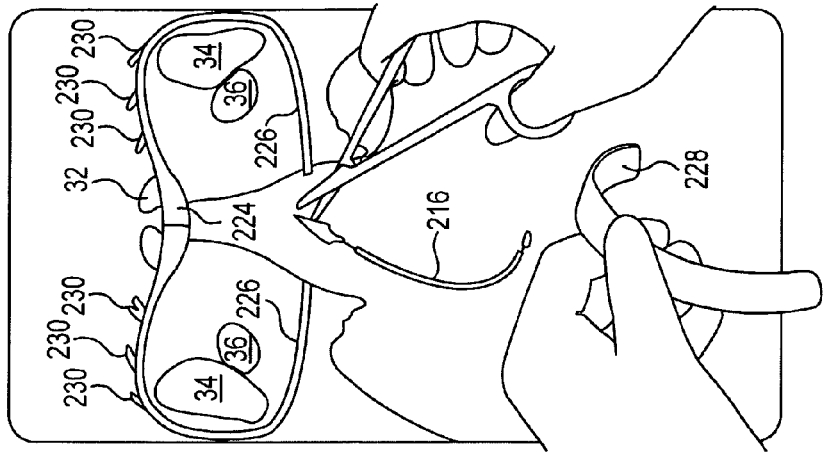
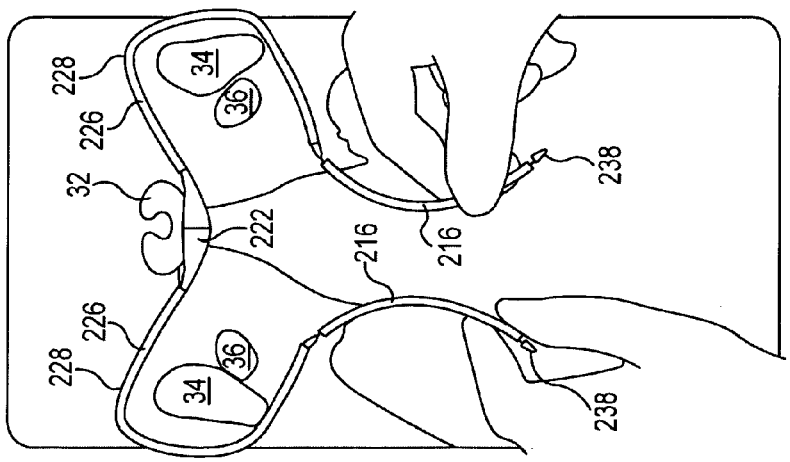
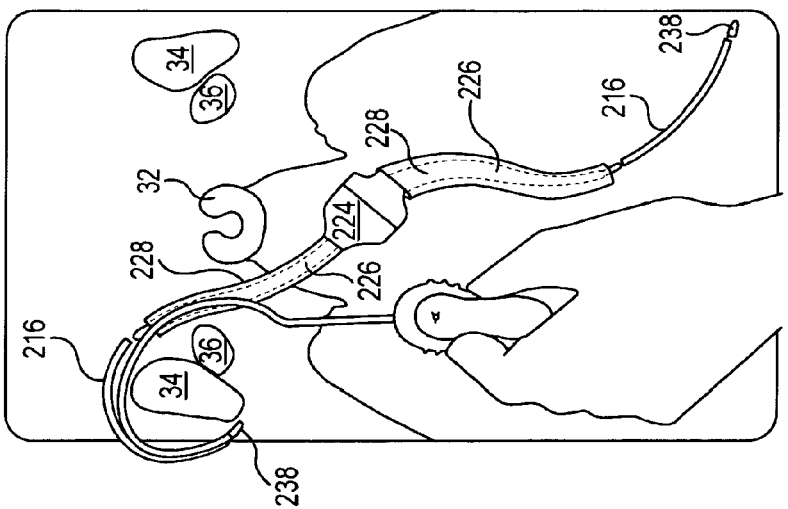

SURGICAL ARTICLES AND METHODS

PRIORITY CLAIM

This application claims the benefit from International No. PCT/US2011/025917, which was granted an International. Filing Date of Feb. 23, 2011, which in turn claims priority under 35 USC §119(e) from U.S. Provisional Patent Application having Ser. No. 61/307,264, filed Feb. 23, 2010, by Wirbisky et al., entitled SINGLE INCISION SLING AND METHOD THEREFOR, which applications are incorporated herein by reference in their entireties.

FIELD OF THE INVENTION

The invention relates to apparatus and methods for treating urinary incontinence by use, of an implant to support urethral tissue.

BACKGROUND

Men, women, and children of all ages can suffer from urinary incontinence or involuntary loss of urinary control. Their lives are perpetually interrupted by thoughts of ensuring that they have ready access to a restroom. Everyday activities such as attending a theater or sporting event can become unpleasant. Sufferers often begin to avoid social situations in an effort to reduce the stress associated with their condition.

A variety of treatment options are currently available. Some of these include external devices, behavioral therapy (such as biofeedback, electrical stimulation, or Kegel exercises), prosthetic devices, and surgery. Depending on the age, medical condition, and personal preference of a patient, surgical procedures can be used to completely restore continence.

One type of surgical procedure found to be an especially successful treatment option for incontinence in both men and women is a sling procedure. Sling procedures typically entail surgically implanting a biocompatible implant or "sling" to support the bladder neck or urethra. Sling procedures are discussed in U.S. Pat. Nos. 5,112,344; 5,611,515; 5,842,478; 5,860,425; 5,899,909; 6,039,686; 6,042,534; 6,110,101; 6,478,727; 6,638,211; and PCT Publication Nos. WO 02/39890 and WO 02/069781.

Some "pubomedial" sling procedures involve an abdominal incision and installation of a sling between the rectus fascia in the abdominal region to a position below the urethra, and back again to the rectus fascia. A conventional procedure in females is to surgically place a sling by entering the abdominal cavity through an incision in the patient's pubovaginal region.

In males, one example of a conventional method involves surgical placement of a sling by entering the abdominal cavity through an abdominal incision. Unfortunately, to access the abdominal cavity a surgeon must incise the male patient's abdominal muscles. This procedure is more time consuming and uncomfortable for the male patient.

Other methods for treating pelvic conditions involve installation of a sling below the urethra through incisions made at the inner thigh (e.g., in the perineal skin facing the obturator and in the groin), and using a tissue path extending through the obturator. These procedures can be referred to as "transobturator" methods. See, e.g., U.S. Pat. No. 6,911,003 and Published U.S. Pat. Appl. No. 2003/0171644A1, the entireties of each being incorporated herein by reference.

While abdominal and transobturator methods of treating urinary incontinence can be effective, safe, and long-lasting, there is ongoing effort toward improving these methods.

SUMMARY

The invention relates to methods of treating pelvic conditions, e.g., urinary incontinence, in males and females.

Certain embodiments of methods and implants involve placement of a tissue support portion of an implant below a urethra, preferably with placement of extension portions of the implant at tissue paths that extend from a location to support the urethra in a direction toward an obturator foramen. A tissue path may extend toward and end at pelvic fascia without reaching or passing into or through the obturator foramen. In other embodiments a tissue path may extend to the obturator foramen. In still other embodiments the tissue path may extend through an obturator foramen. The methods can involve two opposing tissue paths, as described, one on each of a left and a right side of the patient.

The implant may involve an adjustment feature that allows placement of the implant followed by or along with adjustment of the positioning or size of the implant, such as one or more adjustable extension portion. The adjustment feature may be a one-way adjusting engagement, a two-way adjusting engagement feature, a two-way adjusting feature that additionally includes a locking feature, etc. A method may involve adjusting the size of the implant by use of an adjusting feature or adjusting engagement between an extension portion and a support portion. The implant may be placed and optionally adjusted by use of a tool that can contact an implant to allow manipulation of the implant; optionally at the same time the tool may allow for or may be used to provide movement or approximation of tissue to be supported by the implant (e.g., tissue of a urethra).

In one aspect, the invention relates to a system for treating urinary incontinence, the system including a multi-piece implant comprising a support portion piece and an extension portion piece, and an adjusting tool. The support portion piece comprises a tissue support portion sized and shaped for placement to support a urethra. The extension portion piece comprises a proximal end, a distal end, and a tissue fastener, and is adjustably connected to the support portion piece at an adjusting engagement. The adjusting tool comprises a surface capable of engaging the support portion piece, and a moveable holder capable of holding the proximal end of the extension portion piece and moving the proximal end relative to the adjusting engagement.

In another aspect the invention relates to a system for treating a pelvic condition such as urinary incontinence, the system comprising an implant and a tool. The implant comprising a support portion, two extension portions, and two self-fixating tips, one self-fixating tip at an end of each extension portion, and a guide engaged with at least one of the self-fixating tips. The tool includes a shaft having a distal end capable of engaging the self-fixating tip, and a release mechanism at the distal end, the release mechanism capable of selectively engaging and releasing the self-fixating tip. The shaft is capable of engaging the guide to allow the shaft to be led along the guide to become engaged with the self-fixating tip.

In another aspect the invention relates to a system for treating a pelvic condition incontinence. The system includes an adjustable implant comprising a support portion, two extension portions, and two self-fixating tips. One self-fixating tip is located at an end of each extension portion. At least one self-fixating tip is moveably engaged with one of the two extension portions. The support portion being is movable to adjust a location of the support portion along the implant between the self-fixating tips.

In another aspect the invention relates to a system for treating urinary incontinence, the system comprising a multi-piece implant comprising a support portion piece and two extension portion pieces, and an adjusting tool. The support portion piece comprises a tissue support portion sized and shaped for placement to support a urethra. The extension portion pieces each comprise a proximal end, a distal end, and a tissue fastener. The first extension portion piece is adjustably connected to the support portion piece at a first adjusting engagement. The second extension portion piece is adjustably connected to the support portion piece at a second adjusting engagement. The adjusting tool comprises two adjusting surfaces, the two adjusting surfaces being capable of engaging the support portion piece in a manner to place tension along a length of the support portion piece.

In yet another aspect the invention relates to a system for treating urinary incontinence, the system comprising an implant and a tool. The implant comprises a support portion, two extension portions, and a self-fixating tip at a distal end of each extension portion. The tool comprises a proximal end and a distal end, a surface at the distal end capable of approximating a urethra, two shafts that can be extended and retracted from the distal end, and an adjusting surface at each shaft distal end, each adjusting surface being capable of engaging a self-fixating tip.

In another aspect the invention relates to a system for treating urinary incontinence, the system comprising a multi-piece implant comprising a support portion piece and an extension portion piece, and an adjusting tool. The support portion piece comprises a tissue support portion sized and shaped for placement to support a urethra. The extension portion piece comprises a proximal end, a distal end, and a tissue fastener, and is adjustably connected to the support portion piece at an adjustable connection. The adjusting tool comprises a surface capable of engaging the support portion piece.

In another aspect the invention relates to a method of treating urinary incontinence in a male or a female patient. The method includes providing a system according as described herein, placing the implant below a urethra of the patient, and placing tissue fasteners at supportive tissue. Optionally the placement of the implant can be adjusted, the size of the implant or an extension portion can be adjusted, and the method can include using a tool to approximate tissue of the urethra.

BRIEF DESCRIPTION OF THE FIGURES

FIGS. 4A, 4B, and 4C illustrate an exemplary method useful with a described system.

FIGS. 14A, 14B, and 14C illustrate an exemplary method useful with a described system.

DETAILED DESCRIPTION

Figure 1:
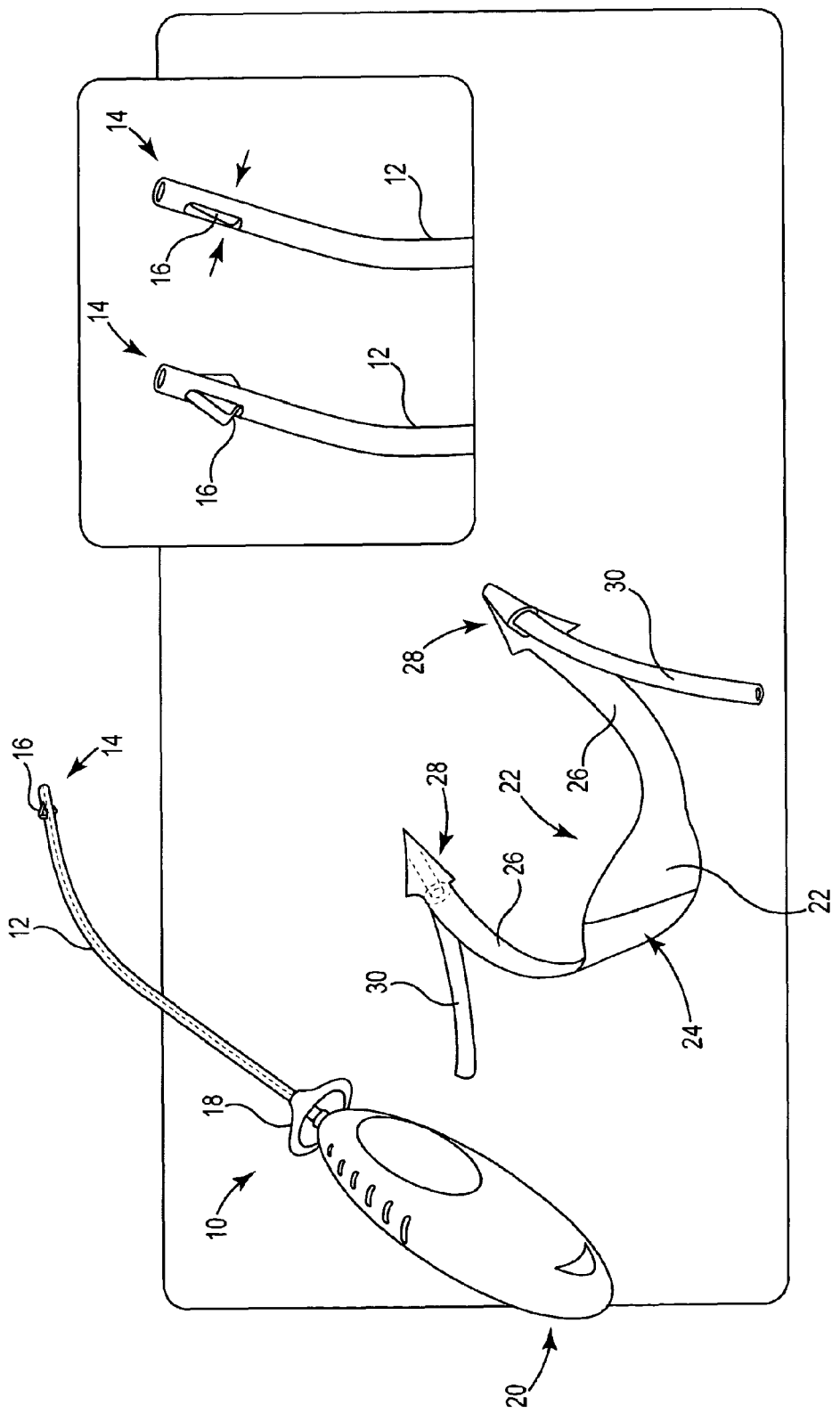
FIG. 1 illustrates an embodiment of a system as described, including a tool and an implant.

The systems, devices, tools, implants, etc., described herein are directed to surgical instruments, assemblies, implantable articles, systems and related methods for treating urinary incontinence in a male or female, including stress urinary incontinence (SUI). An implant can be implanted in a male or a female to treat a condition such as urge incontinence, mixed incontinence, overflow incontinence, functional incontinence, and the like.

An implant can include a tissue support portion (or "support portion") that can be used to support a urethra or other pelvic tissue. Supporting a "urethra" refers to supporting tissue that includes the urethra (which can refer to the bladder neck) and that can optionally include tissue adjacent to a urethra such as bulbospongiosus muscle, corpus spongiosum, or both. According to various methods, for example, a support portion may either be placed below bulbospongiosus muscle to support both bulbospongiosus muscle and corpus spongiosum (along with the urethra), or alternately bulbospongiosus muscle may be dissected and a support portion may be placed to contact corpus spongiosum tissue (to support the urethra).

An implant can additionally include one or more extension portion (otherwise known as an "end" portion or "arm") attached or attachable to the tissue support portion. Normally, for treating incontinence, an implant can include two opposing extension portions. Extension portions are elongate pieces of material (e.g., mesh, suture, or biologic material) that extend from the tissue support portion and either are or can be connected to the tissue support portion, and are useful to attach to anatomical features or "supportive tissue" in the pelvic region (e.g., using a self-fixating tip or another form of tissue fastener) to thereby provide support for the tissue support portion and the supported tissue. Generally for treating incontinence, two extension portions can extend from the opposite ends of a tissue support portion as elongate "ends," "arms," or "extensions," and may attach to supportive tissue in the pelvic region by extending through a tissue path to an internal anchoring point (see, e.g., Applicant's copending United States Patent Application Publication number US 2010/256442, filed Aug. 8, 2008, by Ogdahl, entitled SURGICAL ARTICLES AND METHODS FOR TREATING PELVIC CONDITIONS, the entirety of which is incorporated herein by reference), or may extend to an external incision, such as through an obturator foramen and through an external incision at a groin or inner thigh (see, e.g., Applicant's copending United States Patent Publication Number US 2006/0287571, the entirety of which is incorporated herein by reference). Also see U.S. Patent Publication number US 2011/0034759 and WO 2010/093421, the entireties of which are incorporated hereby by reference.

In exemplary uses, each extension portion can extend from the location of attachment with the tissue support portion, through pelvic tissue, and optionally be attached to supportive tissue within the pelvic region. For certain procedures the supportive tissue can be tissue adjacent to the urethra such as pelvic fascia; tissue between the urethra and an obturator foramen such as pelvic fascia; or tissue of an obturator foramen such as obturator fascia, obturator internus muscle, obturator membrane, obturator externus muscle, etc. For alternate procedures an extension portion can be sized to extend from the tissue support portion, through an obturator foramen, around a pubic ramus bone, and threaded (subcutaneously) back to a medial location such as near a medial incision.

An implant may include portions, pieces, or sections that are synthetic or of biologic material (e.g., porcine, cadaveric, etc.). Extension portions may be, e.g., a synthetic mesh such as a polypropylene mesh, a suture, a biodegradable suture, etc. The tissue support portion may be synthetic (e.g., a polypropylene mesh) or biologic. Examples of implant products that may be similar to those useful according to the present description, include those sold commercially by American Medical Systems, Inc., of Minnetonka Minn., under the trade names Apogee®, Perigee®, and Elevate® for use in treating pelvic prolapse (including vaginal vault prolapse, cystocele, enterocele, etc.), and Sparc®, Bioarc®, Monarc®, and MiniArc® for treating urinary incontinence.

An example of a particular type of pelvic implant is the type that includes supportive portions including or consisting of a tissue support portion and two opposing extension portions extending from the tissue support portion. An implant that has exactly two extension portions can be of the type useful for treating urinary incontinence. The term "supportive portions" refers to portions of an implant that function to support tissue after the implant has been implanted, and specifically includes extension portions and tissue support portions, and does not include optional or appurtenant features of an implant such as a sheath, tensioning suture, tissue fastener, or self-fixating tip or other type of connector for attaching the implant to an insertion tool.

A preferred implant (e.g., sling) for placement against a corpus spongiosum for treatment of urinary incontinence in a male patient may optionally and preferably include a widened central support to provide increased contact and frictional engagement with the corpus spongiosum. See, for example, Assignee's copending United States Patent Publication Number US 2006/0287571 and U.S. Pat. No. 7,422,557, the entireties of these applications being incorporated herein by reference.

Dimensions of a tissue support portion can be any dimensions useful to support urethra tissue for treating incontinence. A tissue support portion can be of sufficient length to support and optionally partially surround a urethra or urethra-supporting tissue. A width of a tissue support portion may optionally and preferably be greater than a width of extension portions and can be sufficiently wide to increase contact area and frictional forces between a tissue support portion and a tissue in contact with the tissue support portion. Exemplary lengths of a tissue support portion can be in the range from 0.5 to 2 inches, such as from 0.75 to 1.5 inches. Exemplary widths of a tissue support portion can be in the range from 0.4 or 0.5 to 4 centimeters, such as from 1 to 2.5 or 3 centimeters. (A tissue support portion may be part of a support portion piece that includes the tissue support portion and optionally some amount of opposing extension portions extending from ends of the tissue support portion.

Dimensions of extension portions according to the invention can allow the extension portion to reach between a tissue support portion placed to support a urethra (at an end of the extension portion connected to the tissue support portion) and a location at which the distal end of the extension portion attaches to supportive tissue at or about the pelvic region. Exemplary lengths of an extension portion for these embodiments, measured for example between a connection or boundary between the extension portion and the tissue support portion, and a distal end of the extension portion, can be, e.g., from 0.5 to 2.75 inches, preferably from 1.0 to 2.25 inches, and the length can optionally and preferably be adjustable. As described elsewhere herein, a length of an extension portion may be fixed (i.e., the extension portion does not include any form of length-adjusting mechanism). Alternate embodiments of implants may include an adjusting engagement that allows a physician to alter the length of an extension portion before, during, or after implantation.

Implants as described can include a tissue fastener at a distal end or a distal portion of an extension portion, which is the end or portion not attached to a tissue support portion. (The term "distal" as used herein (unless noted otherwise) generally refers to a direction toward a patient and away from a surgeon installing a device.) A tissue fastener at a distal end or portion of an extension portion can be any of various types, including: a self-fixating tip that is inserted into soft tissue and frictionally retained; soft tissue anchors; biologic adhesive; a soft tissue clamp that can generally include opposing, optionally biased, jaws that close to grab tissue; and opposing male and female connector elements that engage to secure an end of an extension portion to tissue. (See International Patent Application No. PCT/US2007/014120, entitled "Surgical Implants, Tools, and Methods for Treating Pelvic Conditions, filed Jun. 15, 2007; U.S. patent application Ser. No. 12/223, 846, filed Aug. 8, 2008, entitled SURGICAL ARTICLES AND METHODS FOR TREATING PELVIC CONDITIONS, now U.S. Publication No. 2010/0256442; U.S. patent application Ser. No. 12/669,099, filed Jan. 14, 2010, entitled PELVIC FLOOR TREATMENTS AND RELATED TOOLS AND IMPLANTS, now U.S. Publication No. 2010/0261955; and WO 2009/075800, the entireties of which are incorporated herein by reference.) An implant may also have one or more extension portion that does not include a tissue fastener, for example if the distal end is designed to be secured to tissue by other methods (e.g., suturing), or is intended to pass through an obturator foramen and a tissue path around a pubic ramus bone, in which case the extension portion may optionally include a connector, dilator, or dilating connector, which connects to an elongate tool that can be used to either push or pull the connector, dilator, or dilating connector through a tissue path (e.g., to a medial incision).

One embodiment of a tissue fastener is a self-fixating tip. A "self-fixating tip" in general can be a structure (sometimes referred to as a soft tissue anchor) connected at a distal end of an extension portion (or extension portion piece) that can be implanted into soft tissue (e.g., muscle, fascia, ligament, etc.)

in a manner that will maintain the position of the self-fixating tip and support the attached implant. Exemplary self-fixating tips can also be designed to engage an end of an insertion tool (e.g., elongate needle, elongate tube, etc.) so the insertion tool can be used to push the self-fixating tip through and into tissue for implantation, preferably also through a medial incision to reach the interior of the pelvic region, e.g., at a location of an obturator foramen. The insertion tool may engage the self-fixating tip at an internal channel of the self-fixating tip, at an external location such as at an external surface of the base, at a lateral extension, or otherwise as desired, optionally in a manner to allow the insertion tool to push the self-fixating tip through an incision in a patient and through and into supportive tissue.

Exemplary self-fixating tips can include one or more lateral extensions that allow the self-fixating tip to be inserted into soft tissue and to become effectively anchored in the tissue. A lateral extension may be moveable or fixed. The size of the self-fixating tip and optional lateral extensions can be useful to penetrate and become anchored into the tissue. Exemplary self-fixating tips are described in Assignee's copending international patent application PCTUS2007/004015, filed Feb. 16, 2007, titled Surgical Articles and Methods for Treating Pelvic Conditions, the entirety of which is incorporated herein by reference. Other structures may also be useful.

According to exemplary embodiments, a self-fixating tip can have structure that includes a base having a proximal base end and a distal base end. The proximal base end can be connected (directly or indirectly, such as by a connective suture) to a distal end of an extension portion. The base extends from the proximal base end to the distal base end and can optionally include an internal channel extending from the proximal base end at least partially along a length of the base toward the distal base end. The optional internal channel can be designed to interact with (i.e., engage, optionally by means of a release mechanism that can be selectively engaged and released) a distal end of an insertion tool to allow the insertion tool to be used to place the self-fixating tip at a location within pelvic tissue of the patient. A self-fixating tip can be made out of any useful material, generally including materials that can be molded or formed to a desired structure and connected to or attached to a distal end of an extension portion of an implant. Useful materials can include plastics such as polyethylene, polypropylene, and other thermoplastic or thermoformable materials, as well as metals, ceramics, and other types of biocompatible and optionally bioabsorbable or bioresorbable materials. Exemplary bioabsorbable materials include, e.g., polyglycolic acid (PGA), polylactide (PLA), copolymers of PGA and PLA.

According to various systems as described, one or more instrument, insertion tool, adjusting tool, or the like, may be incorporated or used with the described implants and methods. Examples of useful tools include those that generally include one or more (stationary or moveable) thin elongate, relatively rigid shaft or needle that extends from a handle. The shaft can be a single elongate shaft or multiple separate elongate shafts extending from the handle, or one or more primary shaft that extends from the handle and that contains multiple branch or "tine" shafts that separate at the end of the primary shaft. The handle is located at a proximal end of the device and attaches to one end (a proximal end) of a shaft. According to some embodiments, a distal end of one or more shaft can be adapted to engage a portion of an implant, such as a tissue fastener (e.g., a self-fixating tip), in a manner that allows the insertion tool to engage and push the tissue fastener through a tissue passage and connect the tissue fastener to supportive tissue of the pelvic region. Examples of this type of tool can be used with a self-fixating tip that includes an internal channel designed to be engaged by a distal end of an insertion tool to allow the self-fixating tip to be pushed into tissue. Other general types of insertion tools will also be useful, but may engage a self-fixating tip or other tissue fastener in an alternate manner, e.g., that does not involve an internal channel.

According to other embodiments, a distal end of a tool (e.g., at one more shaft) can be adapted to engage one or more other portion of an implant, such as support portion, a proximal end of an extension portion, or both. The insertion tool may manipulate a tissue support portion and an extension portion of a multi-piece implant in a manner to allow the tool to adjust the size or positioning of the implant.

Exemplary insertion tools for treatment of incontinence and vaginal prolapse are described, e.g., in U.S. patent application Ser. No. 10/834,943, now U.S. Pat. No. 7,500,945, Ser. No. 10/306,179, now U.S. Pat. No. 7,070,556; Ser. No. 11/347,553, now U.S. Pat. No. 7,422,557; Ser. No. 11/398,368, now U.S. Pat. No. 7,740,576; Ser. No. 10/840,646 now U.S. Pat. No. 7,351,197; PCT application number 2006/028828, published as WO 2007/016083; PCT application number 2006/0260618; WO 2010/093421, and US Patent Publication No. 2010-0256442 the entirety of these documents being incorporated herein by reference.

A tool according to the invention can optionally include a mechanism by which a tissue fastener (e.g., a self-fixating tip) can be securely and releasable engaged with a distal end of an insertion tool such that the tissue fastener can be selectively secured to the distal end mechanically, then selectively released. With a releasable engagement, a tissue fastener (e.g., self-fixating tip) can be released from the distal end by releasing the engagement (e.g., mechanical engagement) by movement of an actuator at the proximal end of the insertion tool, such as at the handle. For example, an internal channel (or external surface) of a self-fixating tip can include an engaging surface designed to engage a mechanism at a distal end of an insertion tool while the self-fixating tip is placed at, on, or over the distal end. As an example, an internal or external surface of a self-fixating tip can include a depression, ring, edge, or ledge, that can be rounded, angular, etc. A mechanical detent such as a pin, ball, spring, deflector, or other surface or extension located at the distal end of the insertion tool can be moved, deflected, or extended relative to the distal end of the insertion tool to contact the surface of the self-fixating tip to securely and releasably hold the self-fixating tip at the distal end of the insertion tool and prevent removal of the tip from the distal end until removal is desired. The detent (or other surface or mechanism) can be cause to extend (or retract) from the distal end of the insertion tool by actuating a trigger or other mechanism located at the proximal end (e.g., handle or a proximal location of a shaft) of the insertion tool, to secure (or release) the self-fixating tip. Upon placement of the self-fixating tip at a desired location during a surgical implantation procedure, the insertion tool operator can release the self-fixating tip by use of the trigger or other mechanism at the handle to disengage the detent and cause the tip to become loose. The insertion tool can then be removed from the tissue path, and the self-fixating tip can remain in a desired implanted location.

Optionally, an implant can include a tissue fastener at a location of a tissue support portion, or at a location along a length of an extension portion. This form of tissue fastener can be in the form of reinforced (e.g., by coating, heat treating, or a reinforcing weave or strip) edge extensions, multiple layers of mesh and edge extensions in an extension portion, etc., as described, for example, at Applicant's copending U.S.

Pat. No. 7,422,557, and Applicant's copending United State's Patent Publication Numbers US 2006/0195011, US 2006/0195007, and US 2006/0195010, all of which are incorporated herein by reference. Other examples include relatively rigid structures such as metal, plastic, or other polymeric or non-polymeric structure that may be shaped to frictionally engage soft tissue, for example to include a tine, hook, chevron, barb, arrow, etc., combinations thereof, or any structure added to an edge or surface of an extension portion to improve fixation within tissue. The structure can have any shape or form that will increase frictional force between the implant and adjacent tissue, such as one or multiple pointed surface directed along a length of an extension portion, toward the tissue support portion, and extending away from a surface or edge of the implant (e.g., extension portion). The tissue fastener can be located at a position of an implant that will result in the tissue fastener being located at supportive tissue such as muscle or fascia when the implant is placed with a midline of the tissue support portion being located below a urethra. For example, a tissue fastener may be located on a tissue support portion or an extension portion of an implant, e.g., as close as 2 or 3 centimeters from a midline of a tissue support portion, and up to a distance that reaches tissue of an obturator foramen when the midline is located below a urethra, e.g., up to 7 centimeter from the midline.

According to various embodiments of implants described herein, an implant can include multiple pieces that are adjustably connected together by an adjusting engagement. A "multi-piece" implant refers to an implant that includes a "support portion piece" and one or multiple "extension portion piece" as separate pieces of the implant. An extension portion piece can be separate from a support portion piece, and the two pieces can be connected through an adjustable engagement. The support portion piece includes a tissue support portion.

An adjusting engagement may be for example a one-way adjusting engagement, a two-way adjusting engagement, or a locking two-way engagement, that allows a portion, piece, or a segment of an implant to be moved relative to another portion, piece, or segment if the implant and adjusted as to length, tension, or positioning. Examples of adjusting engagements are described, for example, in Applicant's copending U.S. patent application Ser. No. 12/308,436, filed Dec. 15, 2008, entitled SURGICAL IMPLANTS AND TOOLS FOR TREATING PELVIC CONDITIONS, now U.S. Publication No. 2011/0112357, and U.S. patent application Ser. No. 12/669,099, filed Jan. 14, 2010, entitled PELVIC FLOOR TREATMENTS AND RELATED TOOLS AND IMPLANTS, now U.S. Publication No. 2010/0261955, the entireties of which are incorporated herein by reference.

Some adjusting engagements can allow two-way movement of one piece relative to another piece (e.g., a "two-way" adjusting engagement). This type of adjusting engagement allows movement of a segment of implant (e.g., of a segment or portion of an extension portion piece) in two directions through an adjusting engagement. The force needed to move the segment of implant in one direction is substantially equal to the force needed to move the segment in the opposite direction, and, optionally, the two-way adjusting engagement does not substantially hinder the movement of a segment of implant through the adjusting engagement with frictional surfaces such as extensions (e.g., "teeth") extending into an aperture through which the segment of implant is moved. As an example, a two-way adjusting engagement may include an open (smooth) aperture that may be circular, oval, square, elongate, or rectangular, such as in the form of a circle, slit, or slot, etc. The aperture may optionally be reinforced by a reinforced perimeter of a shape that is similar to the aperture, such as by a fabric or a polymeric material such as a grommet (e.g., a "loose grommet" or "eyelet"), which may be circular, square, rectangular, or of any desired shape. The reinforced perimeter (e.g., grommet) defines a reinforced aperture through which a segment of implant can pass relatively freely and with the same resistance two different directions.

A two-way adjusting engagement may optionally be capable of an open and a closed (e.g., locked) configuration, the open configuration allowing two-way movement between the pieces, and the closed (or locked) configuration preventing any movement between the pieces. Such an adjusting engagement may be referred to as a locking two-way adjusting engagement, and may include any form of mechanical securement device that can be configured in an open configuration (to allow two-way movement between pieces) and a closed configuration (to prevent movement between pieces). The locking two-way adjusting engagement may be selectively and reversibly moveable between the open configuration and the closed configuration, or may instead initially be an open configuration that, once placed in a closed configuration, cannot be re-configured to the open configuration. Examples of structures that may be part of a locking two-way adjusting engagement include a mechanical clip, staple, stitch, detent, or rivet; any form of spring-loaded or moveable frictional engagement; a non-moveable frictional engagement such as a slot, slit, cleat, or other non-moveable aperture or opening through which a portion of implant can be selectively engaged, released, and re-engaged; a deformable opening, ring, clip, staple, etc., which may be generally open and then permanently closed by mechanical deformation; and the like. One form of exemplary structure may be forceably closed (e.g. by bending a part until permanent deformation or closing a part until some latch or similar feature snaps shut), while others may be biased to close (e.g. a spring-loaded clip is held open until released so it can clamp shut). Changing from an open to a closed orientation could be performed by an independent tool, or may be an additional feature built into the adjustment tool. The clip or alternate opening-closing structure could be attached to larger structure of an adjusting engagement (potentially integrated into its design), or separate (so it could be loaded into the tool).

Other adjusting engagements may allow for one-way adjustment such as shortening of a length of an extension portion. These adjusting engagements can be referred to as "one-way" adjusting engageents, and allow adjustment of a length of an implant portion (e.g., extension portion) in one direction and not (or not easily) in an opposite direction. An exemplary one-way adjusting engagement can include an aperture through which a segment of implant (e.g., a portion of an extension portion piece) can extend, and one or multiple surfaces (e.g., extensions or teeth) that frictionally engage the segment of implant passing therethrough, e.g., by extending into or toward the aperture or otherwise contacting the segment of implant to inhibit movement of the segment of implant relative to the adjusting engagement. The one-way engagement can preferentially allow movement of the segment of implant through the aperture in one direction while inhibiting or preventing movement of the segment of implant in an opposing direction.

In use of a tissue support portion that includes a one-way adjusting engagement such as a round or rectangular grommet, a tissue fastener (e.g., a self-fixating tip) at one end of an extension portion is placed at tissue as desired, and the second (loose) end of the extension portion piece is passed through the one-way adjusting engagement. The engagement is adjusted to place the support portion piece at a desired position (length) of the extension portion piece to provide desired support to a urethra. The one-way adjusting engagement moves easily along the extension portion piece in a direction that tightens the implant against urethra tissue, and does not move easily in the opposite direction. Once placed in position below the urethra and tightened as desired, the support portion piece is prevented from moving along the extension portion piece in the direction to reduce support of the urethra. The extension portion piece may optionally be considered to be "smooth," without any visible frictional surface, or may alternately include bumps, detents, teeth, a jagged surface, or other frictional or mechanical structure to engage opposing structure at a surface of an aperture of the one-way adjusting engagement.

FIG. 1 illustrates a system that includes implant 22 (e.g., for treating male or female urinary incontinence) and insertion tool 10. Implant 22 includes support portion 24, end or extension portions 26, and self-fixating tips 28. Guide collars 30 are engaged with each of self-fixating tips 28. Insertion tool 10 includes shaft 12, distal end 14, proximal end and handle 20, release mechanism (e.g., comprising detents, teeth, or extensions) 16, and trigger 18 located at a proximal region of shaft 12. Trigger 18 can activate and de-activate release mechanism 16 to selectively securely engage and release self-fixating tip 28, relative to distal end 14.

FIG. 1 additionally shows a feature of two guides (e.g., guide tubes) 30, each guide being removably engaged with one of the two self-fixating tips 28. Each guide 30 allows a user to move a distal end of shaft of an insertion tool (e.g., 10) into engagement with a self-fixating tip (e.g., 28). In specific, guide 30 is in the form of a hollow guide tube, having an elongate hollow shaft and two ends, one opening at each end. A distal end opening engages a channel or bore of self-fixating tip 28. The distal end removably engages self-fixating tip 28 through any removable or dis-engageable structure, such as a threaded engagement, a perforated engagement, a frictional engagement, or any other form of engagement that can be broken, disrupted, or disengaged by a separate mechanical mechanism located on tool 10, e.g., between proximal handle 20 and distal end 14.

During use, a distal end of an insertion tool (e.g., distal end 14) can be inserted into a proximal end of a guide tube and guided through the guide tube to engage self-fixating tip 28. The guide allows the distal end to engage the self-fixating tip while the self-fixating tip is engaged with the guide. This allows the distal end to engage the self-fixating tip outside of the patient so a surgeon can use the insertion tool to initially place the self-fixating tip through a medial incision and into engagement with supportive tissue. The initial placement may first be performed, after which the shaft and distal end may be removed from the guide and the patient, and the placement and tension of the self-fixating tip and implant may be tested to determine if adjustment is necessary. If so, the distal end and shaft may be re-engaged with the self-fixating tip previously placed at the tissue by re-inserting the distal end into the guide (which is accessible, e.g., a proximal end can remain outside of the patient) and passing the distal end through the guide to re-engage the distal end with the self-fixating tip. The guide leads the distal end to the self-fixating tip, and the distal end can re-engage the self-fixating tip. The insertion tool can then be used to push the self-fixating tip to a location of deeper penetration into the tissue.

After desired placement of the self-fixating tip, followed by disengagement and optional re-engagement of an insertion tool with the initially-placed self-fixating tip, and adjustment, the insertion tool can be removed from the guide and the guide can be removed from the self-fixating tip (optionally while the distal end is engaged with the self-fixating tip).

Figure 2C:
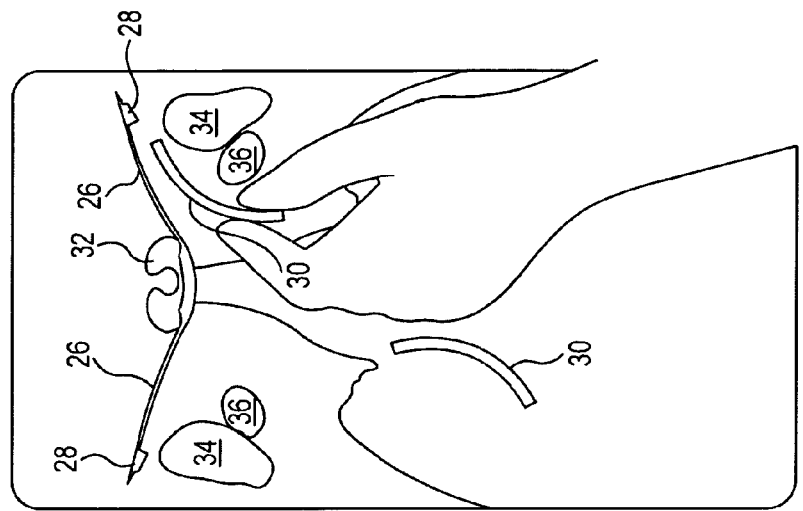
FIGS. 2A, 2B, and 2C illustrate an exemplary method useful with a described system.
Figure 2B:
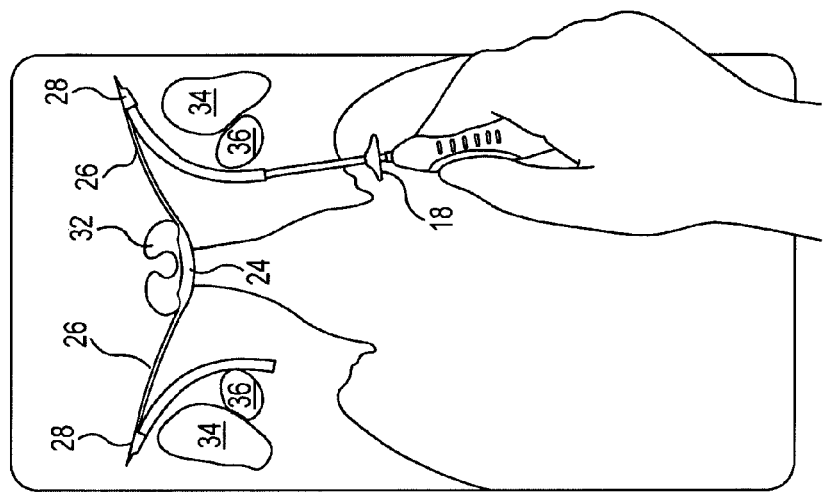
Figure 2A:
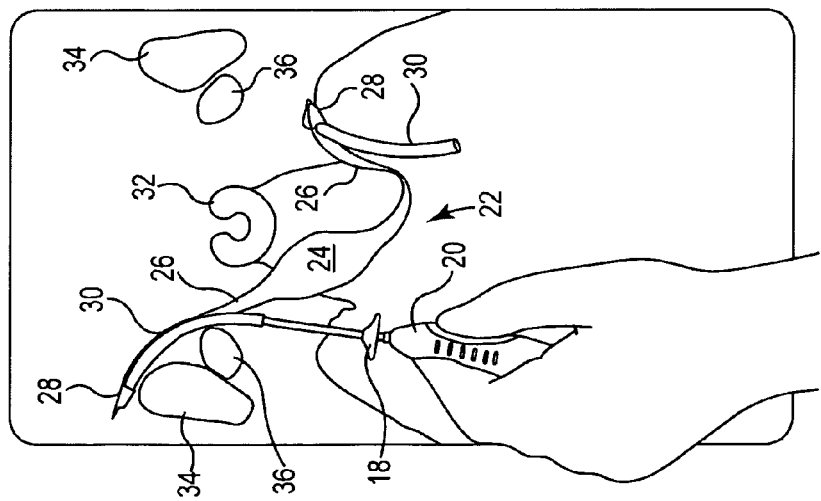

FIGS. 2A, 2B, and 2C, illustrate a method of using tool 10 to place implant 22, with guides 30, to treat urinary incontinence. Patient anatomy includes a medial (e.g., perineal) incision (not shown), a location of a urethra (not shown) and corpus spongiosum 32, corpus cavernosa 36 and pubic ramus bones 34, which bound an obturator foramen (not shown). A distal end of insertion tool 10, passed through guide tube 30 and engaged with self-fixating tip 28, is used to insert self-fixating tip 28 through a medial (e.g., perineal or vaginal) incision and place self-fixating tip 28 at supportive tissue in a region of an obturator foramen on a first side of the patient. See FIG. 2A. Insertion tool 10 is then withdrawn from self-fixating tip 28 and guide tube 30. Release mechanism 16 (e.g., detents) at distal end 14 can be selectively engaged and released as desired. For example, self-fixating tip 28 can be placed in supportive tissue with release mechanism activated to secure tip 28 at distal end 14, and can be de-activated to disengage distal end 14 from self-fixating tip 28 after placement of the tip, followed by withdrawal of shaft 12 away from self-fixating tip 28 and back out of guide tube 30.

As then shown at FIG. 2B, tool 10 can be used to engage the second self-fixating tip 28 of implant 22, through second guide tube 30, and the second self-fixating tip 28 can be placed at supportive tissue in a region of an obturator foramen on a second side of the patient. Tool 10 can optionally be disengaged (by use of trigger 18) from self-fixating tip 28 and withdrawn from guide tube 30.

Optionally tool 10 may be used to adjust the position (e.g., depth) of one or both of self-fixating tips 28 within supportive tissue by re-engaging one or both of self-fixating tips (28) through guide 30 to then push a self-fixating tip 28 to a deeper location within the supportive tissue. The opening at the distal end of each guide tube can be accessible, e.g., extends to a location outside of the patient, while the proximal end of the guide tube and the attached self-fixating tip (28) are located within the supportive tissue (e.g., at a region of an obturator foramen). Upon final adjustment, each of guide tubes 30 can be removed from self-fixating tips 28 and the patient. Removal of a guide tube 30 can optionally be performed with assistance of insertion tool 10. For example, to remove a guide tube 30 from a self-fixating tip, tool 10 can be re-inserted into the guide tube and re-engaged with the self-fixating tip. The tool can engage the self-fixating tip to hold the tip at its location within supportive tissue and prevent undesired (proximal) forces from being applied to the properly-placed self-fixating tip while pressure is placed on the guide tube to separate the guide tube from the self-fixating tip.

Figure 3:
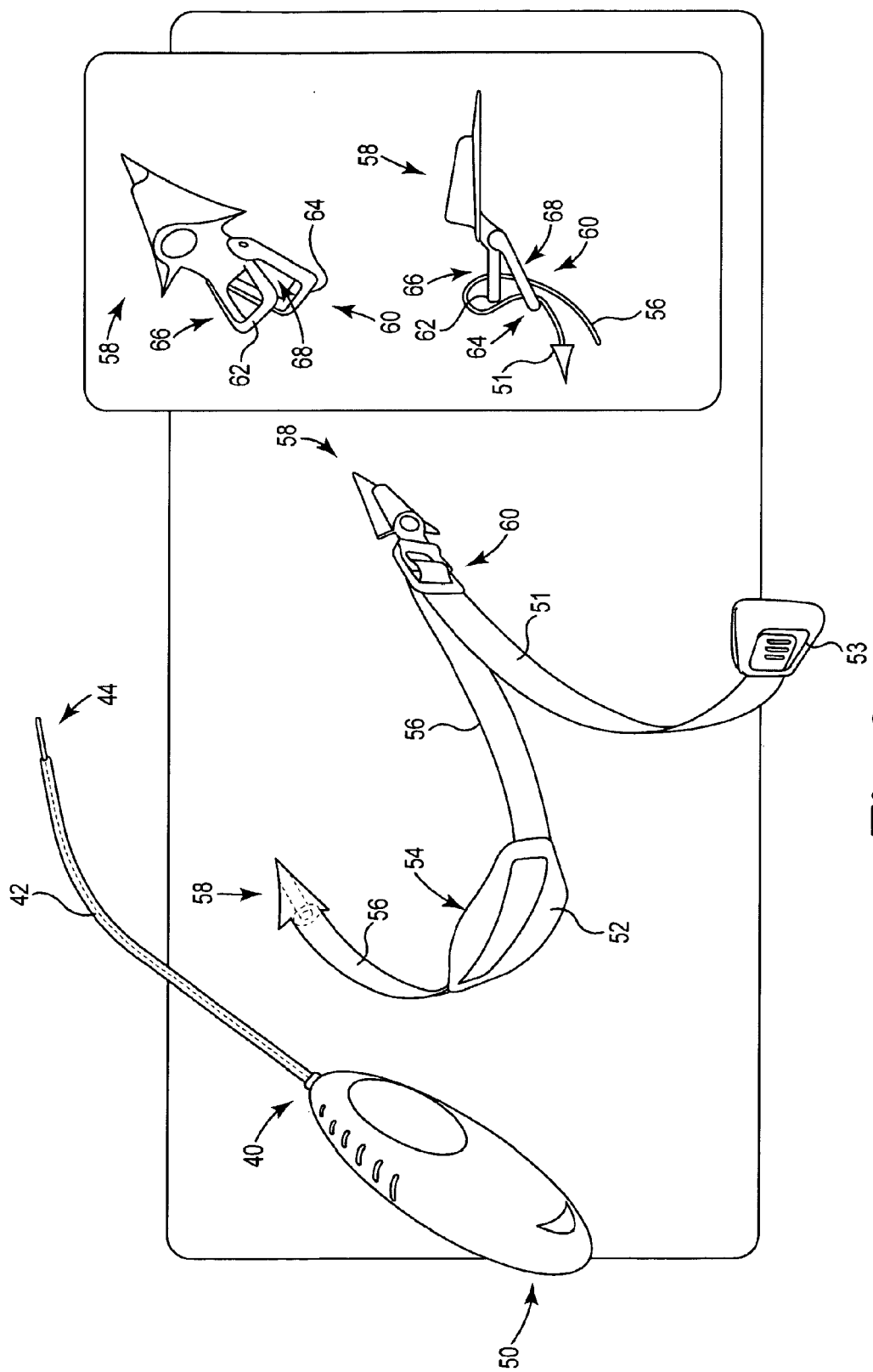
FIG. 3 illustrates an embodiment of a system as described, including a tool and an implant.

FIG. 3 illustrates a system that includes implant 52 (e.g., for treating male or female urinary incontinence) and insertion tool 50. Implant 52 includes support portion 54, two opposing end or extension portions 56, and self-fixating tips 58. Support portion 54 is moveable along the length of the implant between self-fixating tips 58. One of the self fixating tips includes a tightening buckle 60 through which extension portion 56 can be threaded and frictionally engaged. Tightening buckle 60 includes two frictional surfaces, one hinged frictional surface 64 and a second non-hinged frictional surface 62. As illustrated, frictional surface 62 is stationary and frictional surface 64 is hinged to form a frictional engagement that allows for loose end 51 of implant 52 to be pulled (proximally) away from buckle 60, after which, buckle 60 inhibits movement in an opposite direction. In use, a length of extension portion 56 can be threaded initially through hinged loop 68 and stationary loop 66 (see inset at FIG. 3, lower image), adjacent to hinged surface 64 and stationary surface 62, respectively. Extension portion 56 is then threaded back and over stationary frictional surface 62 (outside of loop 66), past hinged frictional surface 64 and through hinged loop 68, to contact the portion of extension portion 56 entering hinged loop 68, then back in a proximal direction (now referred to as loose end 51). Loose end 51 can be pulled to shorten the length of implant located between the two self-fixating tips 58 and to produce a taught length of implant supporting a urethra, after which buckle 60 inhibits loosening or lengthening of the implant within the patient.

Tool 50 includes handle 40, shaft 42, and distal end 44 capable of engaging an aperture of each of self-fixating tips 88. Tool 50 is not specifically illustrated to include a release mechanism like that described with respect to tool 10, but tool 50 could optionally include a release mechanism.

FIGS. 4A, 4B, and 4C, illustrate a method of using tool 50 to place implant 52, having tightening buckle 60 at one end of an extension portion, and adjustable support portion location, to treat urinary incontinence. Patient anatomy is as described previously. A distal end of insertion tool 50, engaged with self-fixating tip 58, is used to insert self-fixating tip 58 through a medial incision and place self-fixating tip 58 at supportive tissue in a region of an obturator foramen on a first side of the patient. See FIG. 4A. Insertion tool 50 is then used to engage the second self-fixating tip 58 for placement of the second self-fixating tip 58 at supportive tissue in a region of an obturator foramen on a second side of the patient. Loose end 51 can be accessible (e.g., can extend out of the medial incision) and can be pulled (proximally) to adjust a length of implant between self-fixating tips 58, to provide desired tension on the length of implant, and desired approximation, placement, and support of the urethra. See FIG. 4B. Loose end 51 can then be removed by cutting. See FIG. 4C. Before, after, or simultaneously with tightening the length of implant by pulling loose end 51, moveable support portion 54 can be moved (slid) in a direction toward one or the other obturator foramen to place moveable support portion 54 at a desired (central, medial) location below the urethra.

Figure 5:
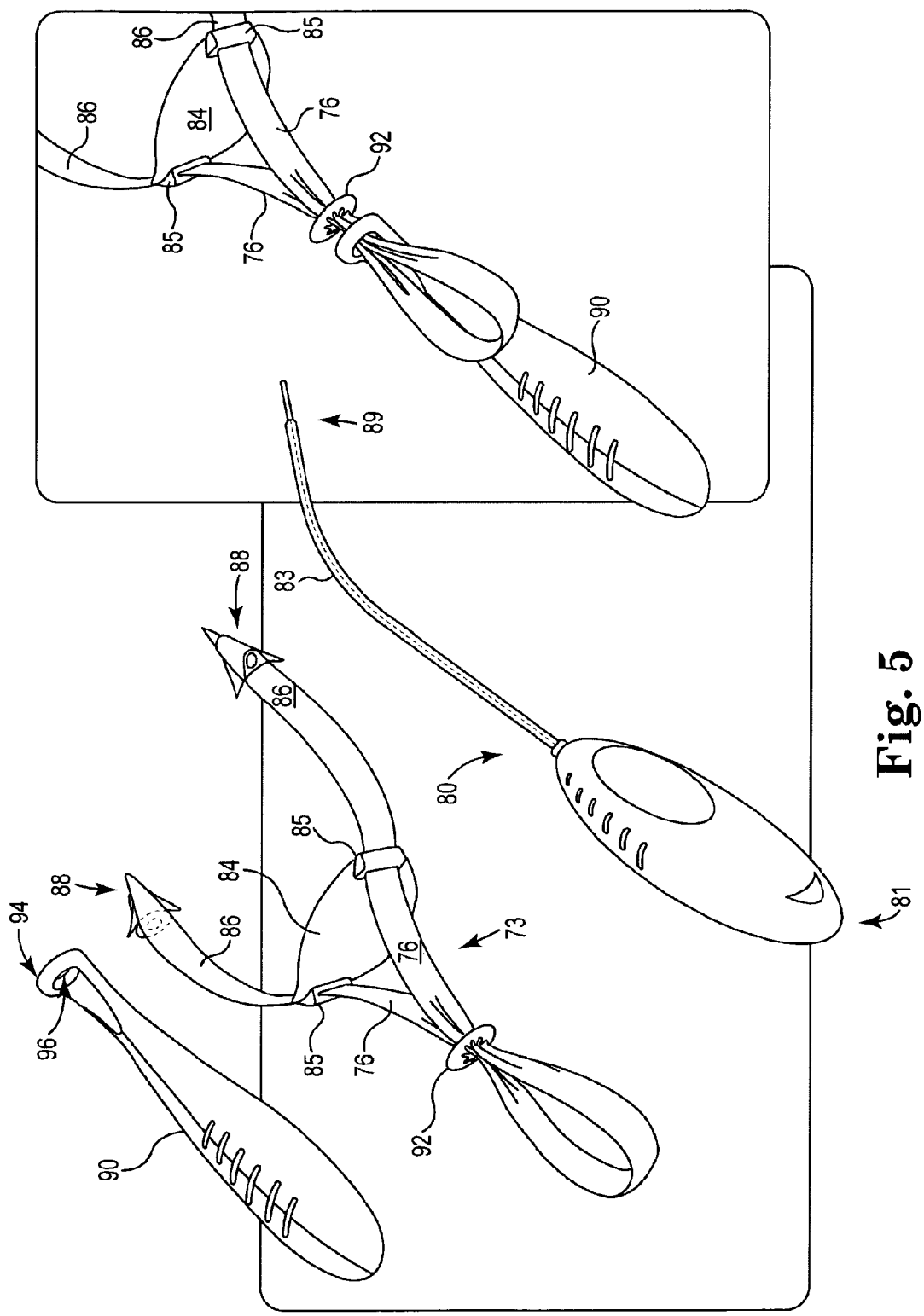
FIG. 5 illustrates an embodiment of a system as described, including a tool and an implant.

FIG. 5 illustrates a system that includes implant 73 (e.g., for treating male or female urinary incontinence) and insertion tool 80. Implant 73 includes support portion 84, end or extension portions 86, and self-fixating tips 88. Support portion 84 is moveable along the length of the implant between self-fixating tips 88. Extension portions 86 extend through supports (or guides) 85 located on support portion 84, allowing each support (or guide) 85 of support portion 84 to be moved and positioned at a desired location along a length of each extension portion 86. The effect is to allow a user to reduce or increase (i.e., lengthen) the effective size of each extension portion by sliding each support 85 toward a respective self-fixating tip 88, on one or both sides of the implant and patient, thereby reducing the overall length of implant 73 between self-fixating tips 88. Support (guide) 85 supports extension portion 86 by means of a one-way or a two-way adjusting engagement.

Upon desired adjustment, locking disk 92 can be moved distally (toward the patient and toward support portion 84 and self-fixating tips 88) along proximal portions (or loop) 76 of extension portions 86, to secure the location of support portion 84 relative to extension portions 86. Locking disk 92 can be frictionally secured to proximal portions 76 to prevent movement of support portion 84 relative to extension portions 86 after desired placement of locking disk 92 relative to proximal portions 76. Optionally an adjusting tool 90 (or "disk pusher tool" 90) can be used to push disk 92 along lengths of proximal portions 76 and toward support portion 84. Proximal portions 76 can be threaded through aperture 96 at a distal end of tool 90, and distal surface 94, which surrounds aperture 96, can contact a proximal surface of disk 92 to push disk 92 distally along proximal portions 76 and toward support portion 84.

Tool 80 includes handle 81, shaft 83, and distal end 89 capable of engaging an aperture of each of self-fixating tips 88. Tool 80 is not illustrated to include a release mechanism like that described with respect to tool 10, but tool 80 could optionally include a release mechanism.

Figure 6C:
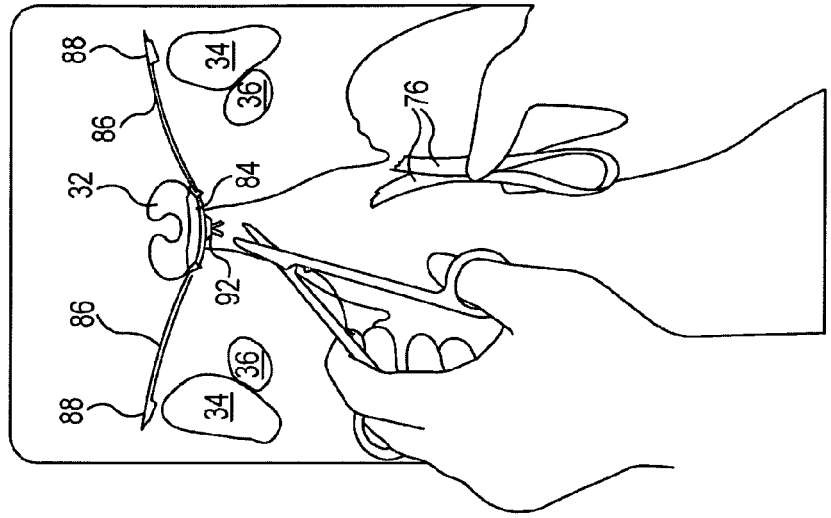
FIGS. 6A, 6B, and 6C illustrate an exemplary method useful with a described system.
Figure 6B:
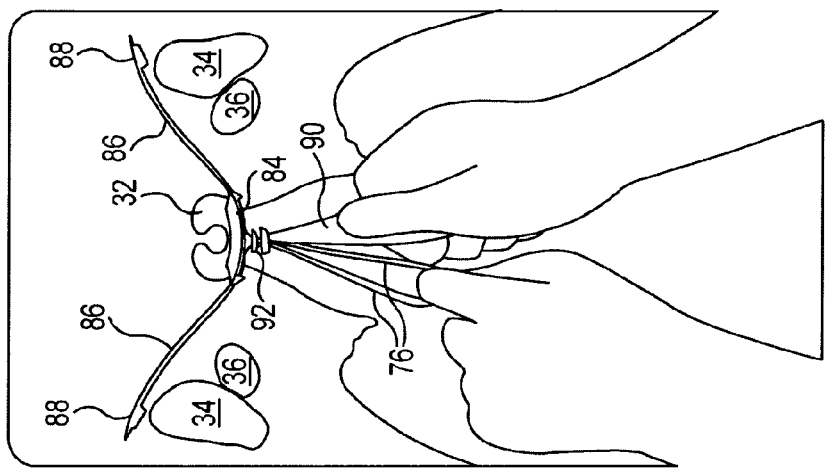
Figure 6A:
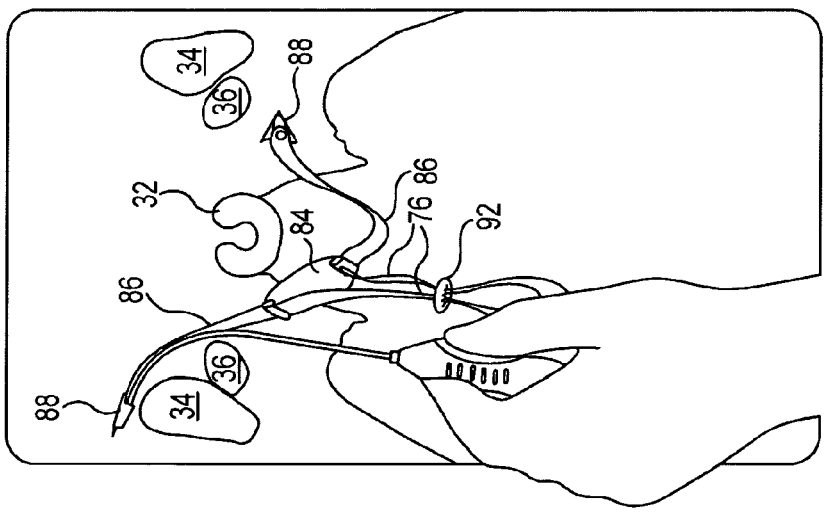

FIGS. 6A, 6B, and 6C, illustrate a method of using tools 80 and 90 to place implant 73, having adjustable support portion 84 and adjustable-length extension portions 86, to treat urinary incontinence. Patient anatomy is as described previously. Distal end 89 of insertion tool 80, engaged with self-fixating tip 88, is used to insert self-fixating tip 88 through a medial incision and place self-fixating tip 88 at supportive tissue in a region of an obturator foramen on a first side of the patient. See FIG. 6A. Insertion tool 80 is then used to engage the second self-fixating tip 88, and the second self-fixating tip 88 can be placed at supportive tissue in a region of an obturator foramen on a second side of the patient. Proximal portions 76 can be pulled or tensioned (optionally with insertion tool 80 engaged with a self-fixating tip 88, to prevent force being placed on the self-fixating tip) while adjustable support portion 84 is advanced distally toward the patient to adjust a lengths of extension portions 86 and the length implant between self-fixating tips 88, and to provide desired tension on the length of implant and desired approximation, placement, and support of the urethra. See FIG. 6B. Locking disk 92 (a one-way adjusting engagement relative) can be moved (e.g., slid) distally toward the patient to frictionally engage proximal portions 76 to maintain the position of adjustable support portion 84 relative to extension portions 86 and the urethra. Disk pusher tool 90 can be used to move locking disk 92. Proximal portions 76 can be removed by cutting. See FIG. 6C.

Embodiments of systems, kits, methods, and devices as described also include adjusting tools for simultaneously contacting two surfaces of an implant, especially two spaced surfaces of a support portion piece, e.g., to manipulate or stabilize the support portion piece, to allow adjustment of extension portion pieces relative to the support portion piece. Preferred tools can include two adjusting surfaces that are capable of concurrently (e.g., simultaneously) contacting two spaced surfaces of a support portion piece, each of the two surfaces of the support portion piece being part of, at, or adjacent to a component of an adjusting engagement, e.g., a one-way adjusting engagement or a two-way adjusting engagement that can be closed or locked.

An adjusting tool can include any useful structure to support the adjusting surfaces of the adjusting tool, such as a handle (optional) at a proximal end, a shaft or multiple shafts extending from the handle, or alternate forms of support for the adjusting surfaces. An adjusting surface can be any surface that can contact or otherwise engage a surface of an implant or a component of an implant. Optionally an adjusting surface can be a structure that defines an aperture, slot, opening, channel, peg, slit, extension, insert, or other surface that is sized to engage a opposing or complementary component or surface of a single piece or a multi-piece implant, e.g., an extension portion piece (e.g., a proximal end of an extension portion piece), a support portion piece, or a tissue fastener (e.g., a self-fixating tip). Adjusting surfaces of an adjusting tool can be spaced from each other by a distance that will allow simultaneous contact with two locations on opposing sides of an implant during use of the adjusting tool to position and optionally adjust the position of the implant relative to urethral tissue being supported. For example, adjusting surfaces may be located on a line that is perpendicular to an axis of a shaft of an adjusting tool, or that is perpendicular to a line parallel to an axis of a shaft of a tool, and may be spaced by a distance in the range of 0.5 to 10 centimeters, such as a distance in the range from 2 to 8 centimeters or from 2 to 6 centimeters (depending on the locations of the implant that the adjusting surfaces are intended to contact). Optionally, the adjusting surfaces can be either stationary or moveable (e.g., extendable away from another component of the adjusting tool such as a handle or a primary shaft.

In certain embodiments, each of two adjusting surfaces can be located at an end of a single or of two separate shafts extending from a handle. In particular embodiments a single (e.g., primary) shaft may extend from a handle, two separate tines or extensions can extend in different directions from the single shaft at a distal location, and one adjusting surface can be at an end of each tine (or "extension"). For example, an adjusting tool may include a handle, a single shaft, and a "yoke" fixed or movably located at a distal end of the shaft; the yoke can extend in two directions from the shaft and can include one adjusting surface at the end of each extension. A line that connects the adjusting surfaces may be located to intersect a longitudinal axis of the shaft (the shaft, shaft extensions, and adjusting surfaces are contained in a single plane), or, in alternate embodiments, a line that connects the adjusting surfaces may be located to not intersect a longitudinal axis of the shaft (the shaft, shaft extensions, and adjusting surfaces are not contained in a single plane).

The adjusting surfaces can optionally be fixed or may be moveable, e.g., relative to a shaft or a handle of the tool. The adjusting surfaces may be fixed, or may be capable of being moved relative to a shaft or handle in a manner to allow the adjusting surfaces to contact and adjust an implant by contacting opposite ends of an implant (opposite self-fixating tips) or opposite ends of a piece of an implant (e.g., a support portion piece or an extension portion piece) simultaneously. For example, the adjusting tool may include a handle, a single shaft, and a "yoke" that can be stationary or that can be moved along a length of the shaft, the yoke extending in two directions from the shaft and including one adjusting surface at the end of each extension.

A distal end of a handle, shaft, or other feature of an insertion or adjusting tool may optionally be designed to contact tissue of a urethra to assist in approximating the urethra. For example, a distal end of a handle or a shaft may optionally be adapted to contact a urethra during placement or adjustment of an implant, for example by having a curved (e.g., concave) or a flat surface that approximates or matches a shape of a surface of urethral tissue (e.g., at a bulbospongiosus muscle or a corpus spongiosum) to be supported by the tissue support portion of the implant being adjusted.

Figure 7:
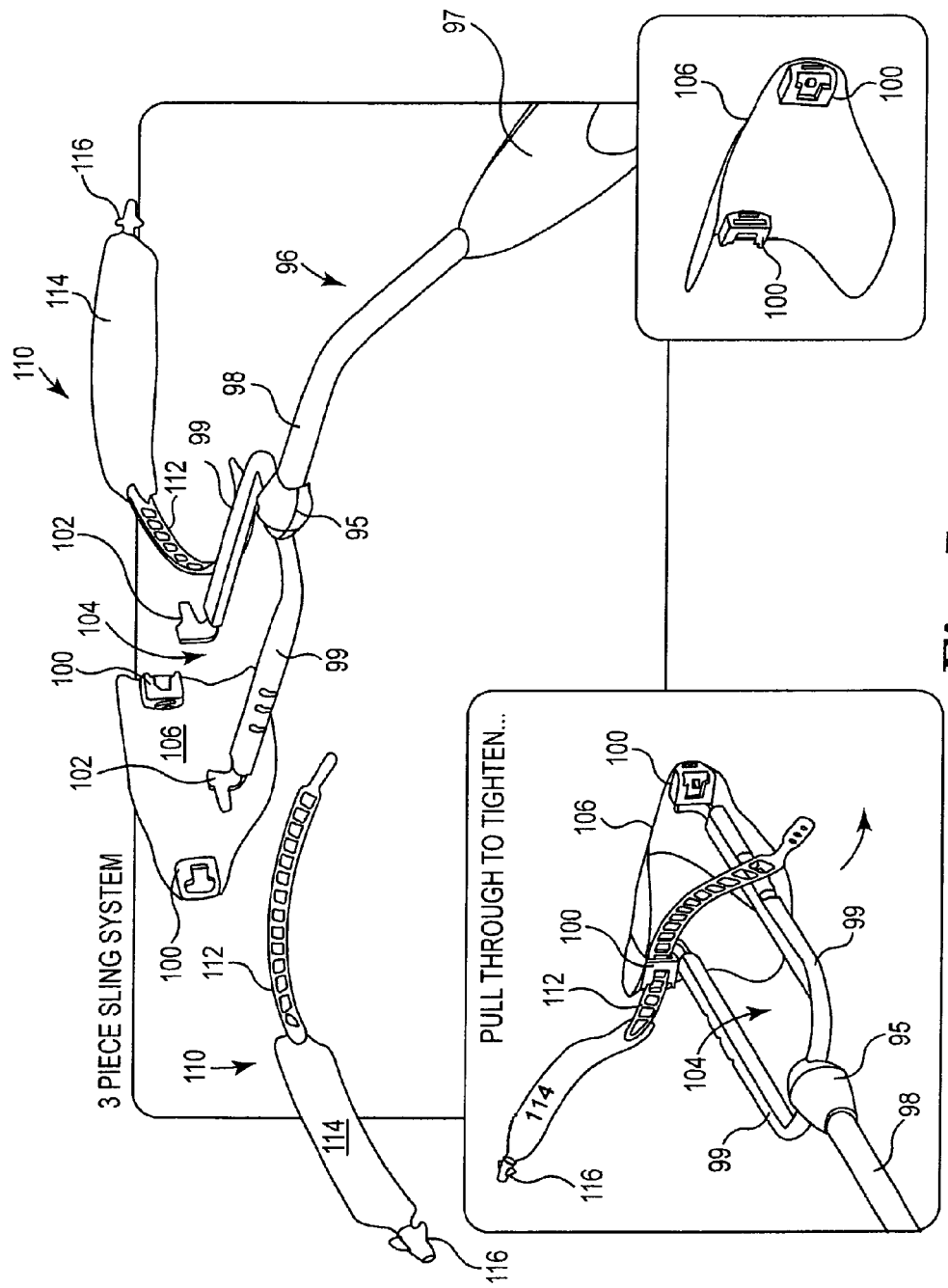
FIG. 7 illustrates an embodiment of a system as described, including a tool and an implant.

FIG. 7 illustrates a system for treating urinary incontinence, the system comprising a multi-piece implant and an adjusting tool that includes two distal adjusting surfaces. Adjusting tool 96 includes handle 97, shaft 98 extending from a proximal shaft end at handle 97 to junction 95 where the distal end of shaft 98 meets yoke (alternately opposing "yoke extensions") 99 extending in two directions away from shaft 98. Yoke 99 includes opening (or "gap") 104 between its opposing extensions. Each of the two distal ends of each yoke extension 99 includes adjusting surface 102 that includes an extension (or "prong" or "insert" directed laterally) that is capable of engaging receiver 100.

Each receiver 100 is located at an end of adjustable support portion piece 106, and includes structure to receive adjusting surface 102 as well as a component, portion, or feature of extension portion piece 110. As shown, extension portion piece 110 includes a mesh portion 114, a non-mesh portion 112, and a self-fixating tip 116. Non-mesh portion 112 includes structure that frictionally engages receiver 100 to provide an adjusting engagement as described herein, e.g., a one-way or a two-way adjusting engagement. As illustrated, non-mesh portion 112 includes a slotted or apertured tab that has openings, slots, apertures, or surfaces that engage a one-way ratcheting structure of receiver 100. The distance of separation of surfaces 102 is about equal to the distance of separation of receivers 100, which is approximately the same as the length of support portion 106. To engage the two surfaces 102 of the two opposing yoke extensions 99 with each of the two receivers 100, one surface 102 can be initially inserted into one receiver 100. Yoke 99 can be squeezed together, e.g., by hand, to allow the spacing between surfaces 102 to be reduced, so the second surface 102 can be inserted into second receiver 100. Yoke 99 can be removed from the two receivers 100 in the same manner. The system also includes one or more insertion tool (e.g., 10, 50, or 80) (not shown) for engaging self-fixation tips 116 for placing self-fixating tips 116 into supportive tissue.

Figure 8C:
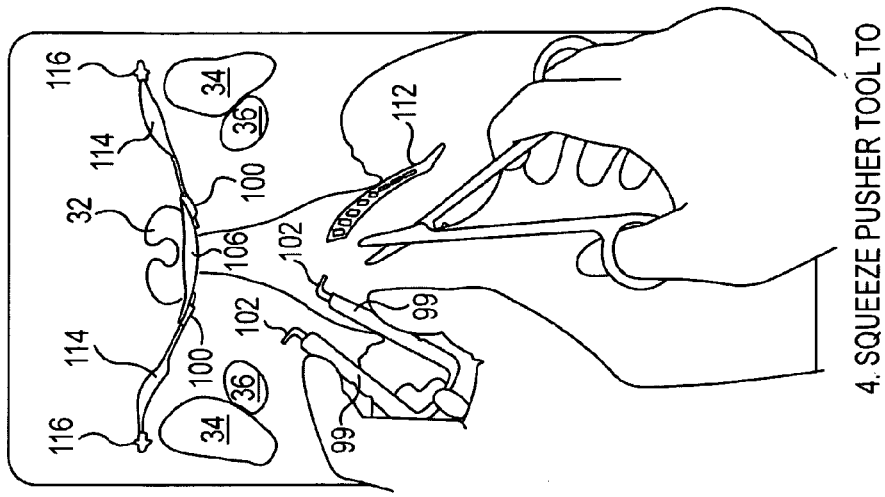
FIGS. 8A, 8B, and 8C illustrate an exemplary method useful with a described system.
Figure 8B:
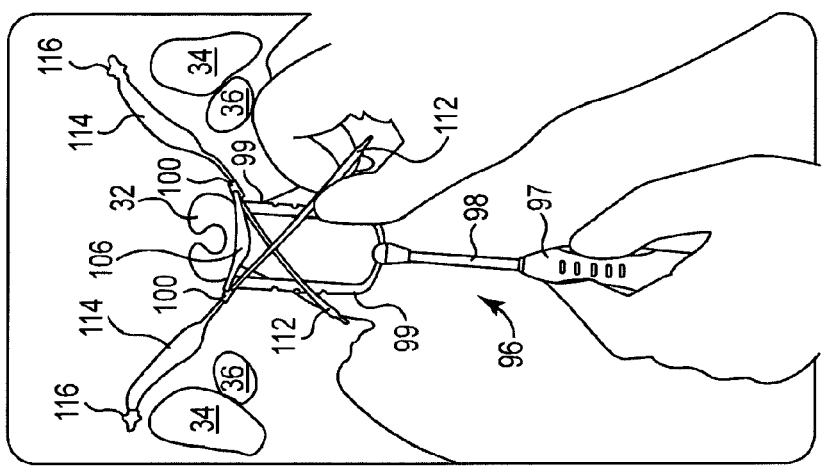
Figure 8A:
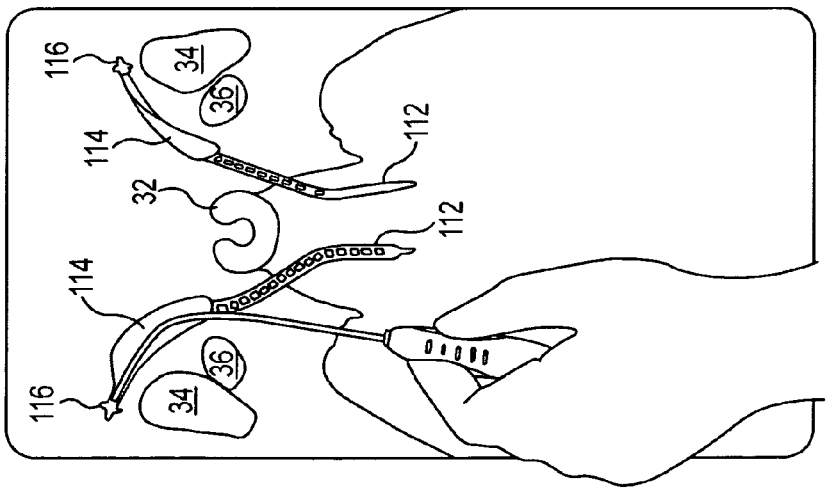

FIGS. 8A, 8B, and 8C, illustrate a method of using tool 96 and an insertion tool (e.g. 10) to place a three-piece implant having adjustable support portion piece 106 and two extension portion pieces 110, to treat urinary incontinence. Patient anatomy is as described previously. A distal end of an insertion tool (e.g., 10, not shown), engaged with self-fixating tip 116, is used to insert self-fixating tip 116 through a medial incision and at supportive tissue in a region of an obturator foramen on a first side of the patient. See FIG. 8A. The insertion tool is then used to engage the second self-fixating tip 116 and place the second self-fixating tip 116 at supportive tissue in a region of an obturator foramen on a second side of the patient.

Non-mesh portions 112 are inserted, one each, into each of the two receivers 100, to assemble an adjusting engagement between receiver 100 and non-mesh portions 112. Adjusting surfaces 102 of tool 96 are then inserted (e.g., with squeezing together of yoke extensions 99) into receivers 100. See FIG. 8B. Each non-mesh portion 112 can be pulled through receiver 100, while tool 96 is used to advance adjustable support portion 84 distally, toward the patient, to adjust lengths of extension portion pieces 110 extending from each receiver 100 to self-fixating tips 116, and to adjust the length of implant between the two self-fixating tips 116, and to provide desired tension on the length of implant and desired approximation, placement, and support of the urethra. See FIGS. 8B and 8C. Tool 96 can be removed, again by squeezing yoke extensions 99 together, allowing surfaces 102 to be removed from receivers 100. Non-mesh portions 112 can be removed by cutting.

Figure 9A:
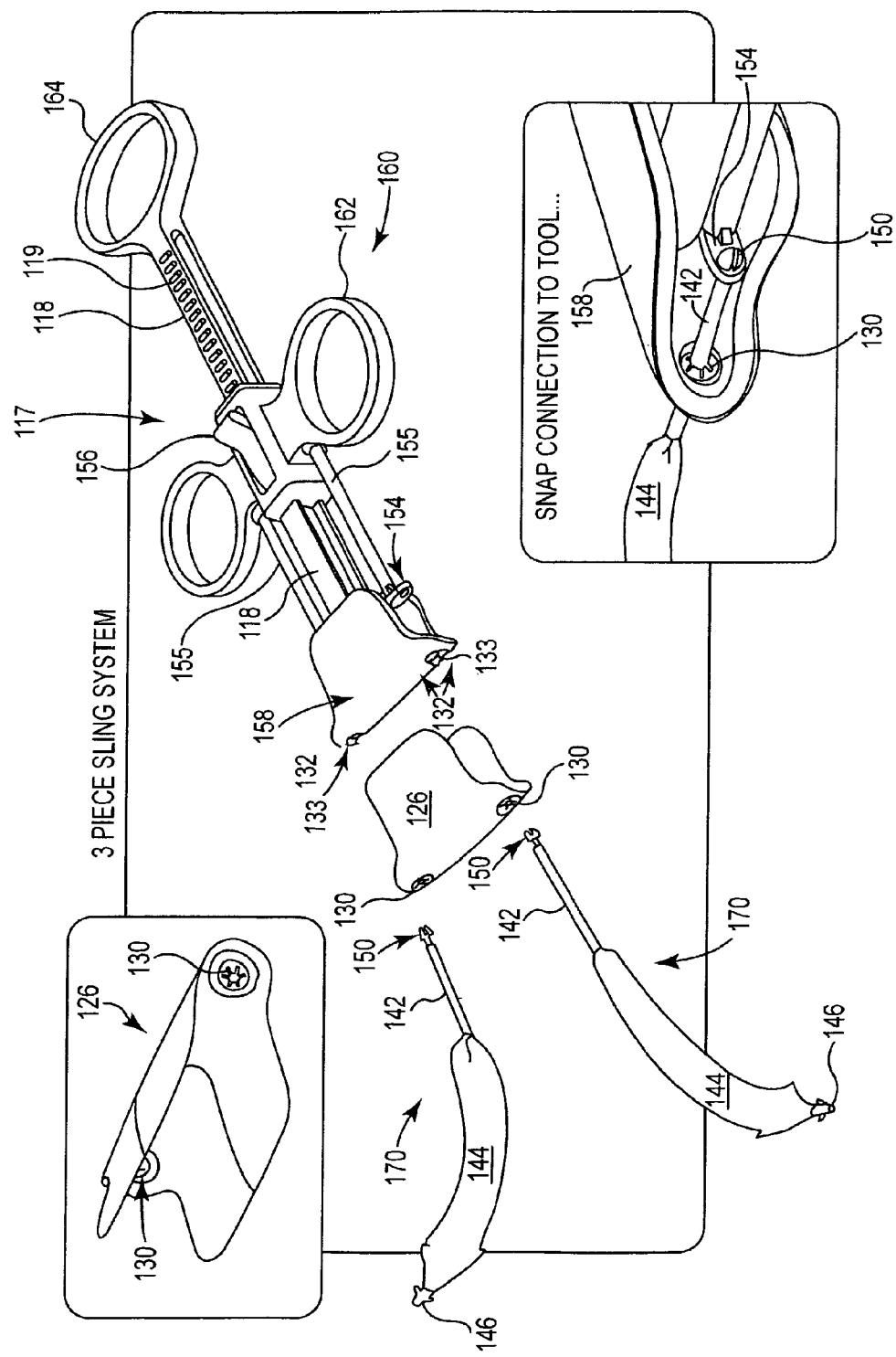
FIGS. 9A and 9B illustrate embodiments of systems as described, including a tool and an implant.

FIG. 9A illustrates a system for treating urinary incontinence, the system comprising a multi-piece implant and a tool that includes two distal adjusting surfaces. Adjusting tool 117 includes handle 160 that includes thumb ring 164 and two finger rings 162. Shaft 118 extends from a proximal shaft end at handle 117, to surface 158, which includes two adjusting surfaces 132 defined adjacent to apertures 133. Curved and lateral surface 158 extending between apertures 133 is sized and shaped to contact and assist in approximating tissue of a urethra (e.g., corpus spongiosum, bulbospongiosus muscle, etc.) during use of tool 117 to place an implant to support the urethra. Secondary shafts 155 extend alongside primary shaft 118. A distal end of each secondary shaft 155 includes snap-fit component 154, capable of receiving complementary snap-fit feature 150 of a proximal end of extension portion piece 170. Shaft 118 and thumb ring 164 are moveable longitudinally relative to finger rings 162, the movement being controlled by a ratcheting mechanism involving teeth 119 and reversible, lockable ratchet switch 156. Secondary shafts 155 are secured to finger rings 162 and will move with finger rings 162 as finger rings 162 are moved longitudinally along primary shaft 118.

A multi-piece implant includes support portion piece 126 and two extension portion pieces 170. Extension portion pieces 170 include a mesh portion 144, a non-mesh portion (or "adjustment portion") 142, a self-fixating tip 146, and a male snap-fit component 150, which can engage female snap-fit component 154. Support portion piece 126 includes a surface to support a urethra and two apertures 130; each aperture 130 can be a component of an adjusting engagement with non-mesh portion 142, e.g., a grommet or other one-way (or two-way, locking) frictional engagement. As illustrated extension portion piece 170 and a distal end of each secondary shaft 155 include opposing snap-fit components to allow the extension portion piece and secondary shaft to be snap-fitted together; any alternative type of connection (e.g., a non-snap-fit mechanical engagement such as a thread, ratchet, etc.) would also be useful. Also as illustrated, snap fit component 154 is a female component (aperture) and snap-fit component 150 is a male snap-fit component (insertable into the aperture of snap-fit component 154). Alternate arrangements would also be useful. Non-mesh portions 142 include structure that frictionally engages aperture 130 to provide an adjusting engagement between aperture 130 and non-mesh portion 142, the adjusting engagement being, e.g., a one-way or a two-way adjusting engagement. As illustrated, non-mesh portion 112 includes a polymeric rod that has surfaces that engage a one-way frictional structure (e.g., grommet) at each aperture 130. The non-mesh portion of this or any other embodiment may alternately be a mesh material or an alternate form of a mesh or a non-mesh material, such as a perforated strip, a slotted strip, a tubular mesh material, or a standard mesh (e.g., mesh strip or mesh tape). A tubular mesh material may be a mesh formed, in any manner, into a tube, such as being woven or knitted into tubular form, or treated with heat (e.g., thermoformed, melted) to form a tubular mesh.

In use, after placing each extension portion piece 170 at a desired patient location, e.g., with self-fixating tips 146 at supportive tissue, support portion piece 126 can be placed over distal surface 158 of tool 117 with apertures 130 seated against apertures 133. Proximal ends of extension portion pieces 170 can be passed through aperture 130 and aperture 133, and engaged with aperture 154 of secondary shaft 155. A user can grasp handle 160 with fingers in finger rings 162 and a thumb at thumb ring 164. Movement of finger rings 162 toward thumb ring 164 causes finger rings 162 to move in a proximal direction relative to (and toward) thumb ring 164. Simultaneously, secondary shafts 154 move proximally relative to primary shaft 118, distal surface 158, and support portion piece 126. In turn, extension portion pieces 170 (engaged with secondary shafts 154) are pulled in a proximal direction relative to support portion piece 126. Surface 158, in contact with support portion piece 126, can be inserted through the medial incision to contact tissue of a region of a urethra, to push or otherwise contact or place pressure on the urethra, to assist in approximating the urethra. The extension portion pieces can then be drawn through apertures 130 (using the tool as described) to adjust the length of the extension portions and the location of the tissue support portion.

Figure 10C:
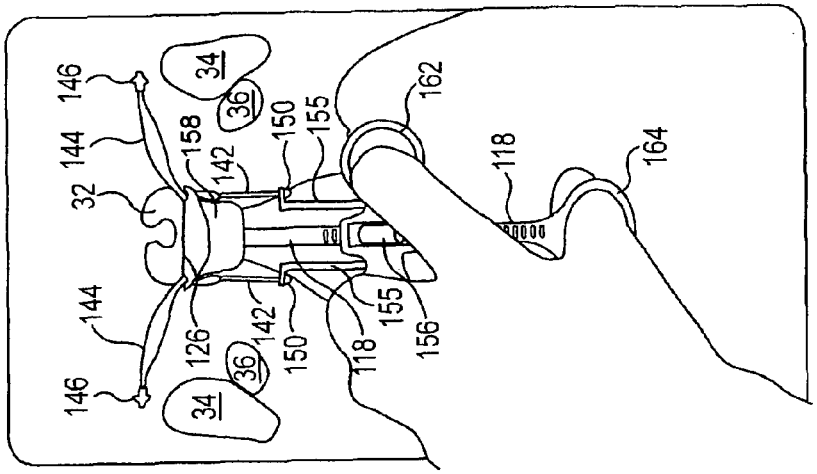
FIGS. 10A, 10B, and 10C illustrate an exemplary method useful with a described system.
Figure 10B:
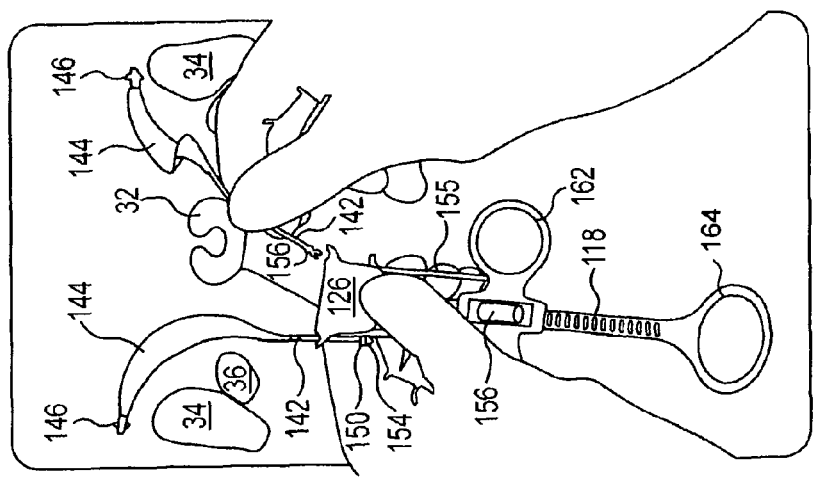
Figure 10A:
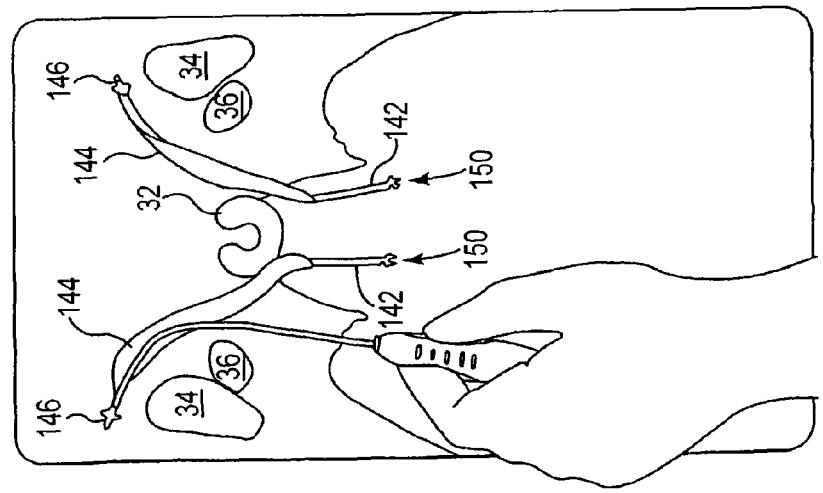

FIGS. 10A, 10B, and 10C, illustrate a method of using tool 117 and an insertion tool (e.g. 10) to place a three-piece implant having adjustable support portion piece 126 and two extension portion pieces 170 to treat urinary incontinence. Patient anatomy is as described previously. A distal end of an insertion tool (e.g., 10, not shown), engaged with self-fixating tip 146, is used to insert self-fixating tip 146 through a medial incision and at supportive tissue in a region of an obturator foramen on a first side of the patient. See FIG. 10A. The insertion tool is then used to place the second self-fixating tip 116 at supportive tissue in a region of an obturator foramen on a second side of the patient.

Non-mesh portions 142 are inserted, one each, through apertures 130 and 133, and snap-fit component 150 is engaged with aperture 154. See FIG. 10B. Finger rings 162 are moved proximally, toward thumb ring 164, to cause secondary shafts 154 move proximally relative to primary shaft 118. Proximal ends of extension portion pieces 170 (engaged with secondary shafts 154) are pulled in a proximal direction relative to support portion piece 126. Surface 158, in contact with support portion piece 126, can contact tissue of a region of a urethra approximate the urethra. Extension portion pieces 170 are drawn through apertures 130 to adjust the lengths of the extension portions 144 and the location of tissue support portion 126. See FIG. 10C. Upon desired placement of the assembled implant and urethra, tool 117 can be removed by cutting a proximal location of each support portion piece 170, e.g., mesh portion or non-mesh portion of support portion piece 170 that has become located on a proximal side of aperture 130.

Figure 9B:
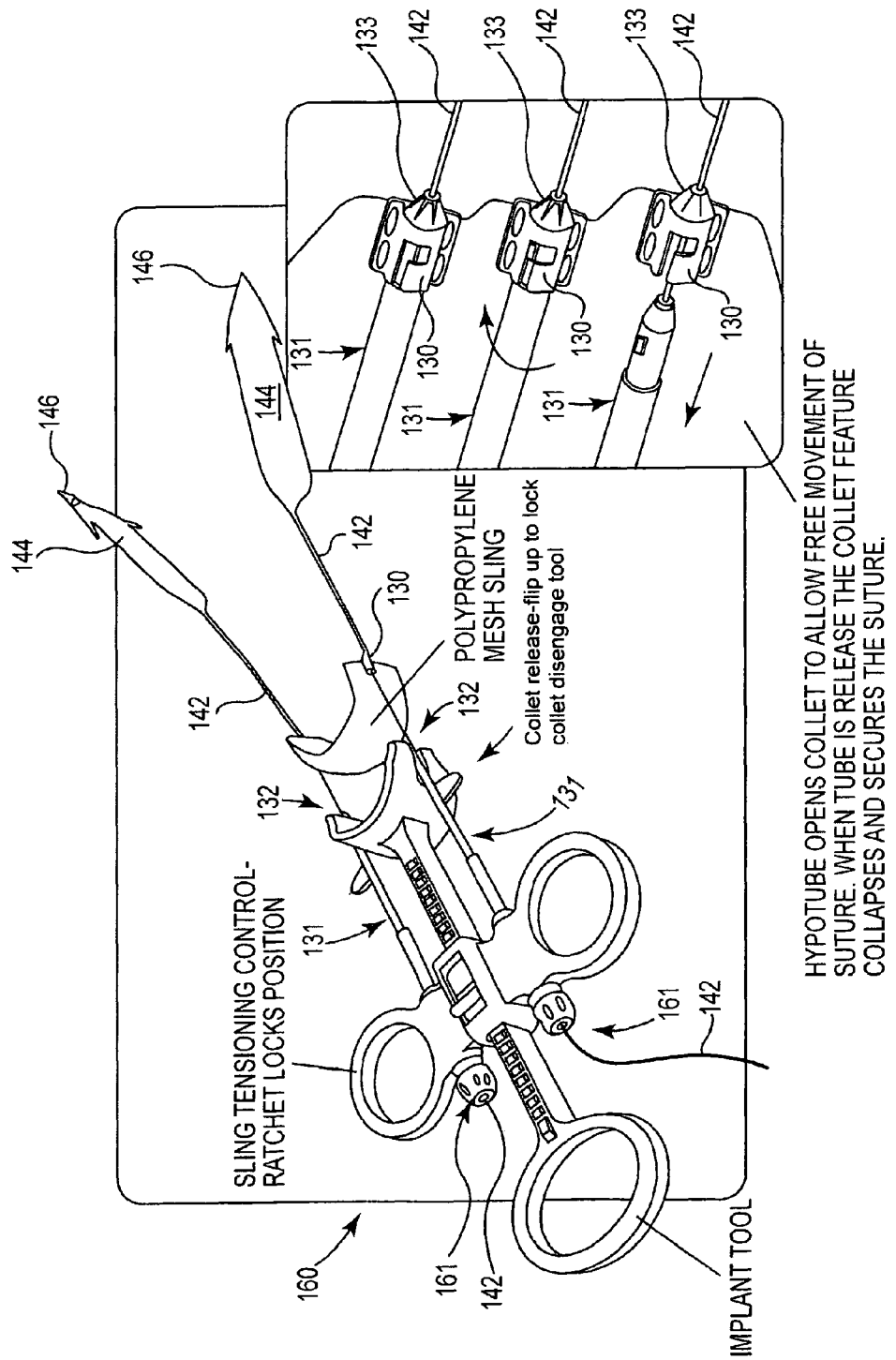

FIG. 9B shows tool 117 and a multi-piece implant, as shown at FIG. 9A, with modifications as follows. Non-mesh portion 142 is a suture that can be threaded collet 133 (or another form of locking two-way adjusting engagement) and suture adjustment and lock 161. Tube 131 seats against collet 133, with locking collet engagement 130; all are near surface 132 and capable of maintaining the position of collets 130 of support portion piece 126 near surface 158. Suture adjustment and lock 161 is a locking or closeable two-way adjusting engagement that can be opened (to form an open two-way adjusting engagement) and closed (to lock non-mesh portion 142 relative to finger rings 162). In use, tube 131 is inserted in a distal direction into locking collet engagement 130, opening collet 133 (see inset). With suture adjustment and lock 161 (both of these) in open configurations, non-mesh portion 142 can be freely moved through each suture adjustment and lock 161. Suture adjustment and lock 161 can be closed to lock suture 142 relative to finger rings 162. Tool 160 can be used to pull non-mesh portions 142 in a proximal direction to adjust the size and position of the implant and urethra. Upon proper adjustment, tube 131 can be removed from collet engagement 130, closing collet 133 and fixing the position of non mesh portion 142 relative to support portion piece 126. Suture adjustment and lock 161 (both of these) can be opened to allow two-way movement of non-mesh portion 142 therethrough, and tool 117 can be removed proximally.

Figure 11:
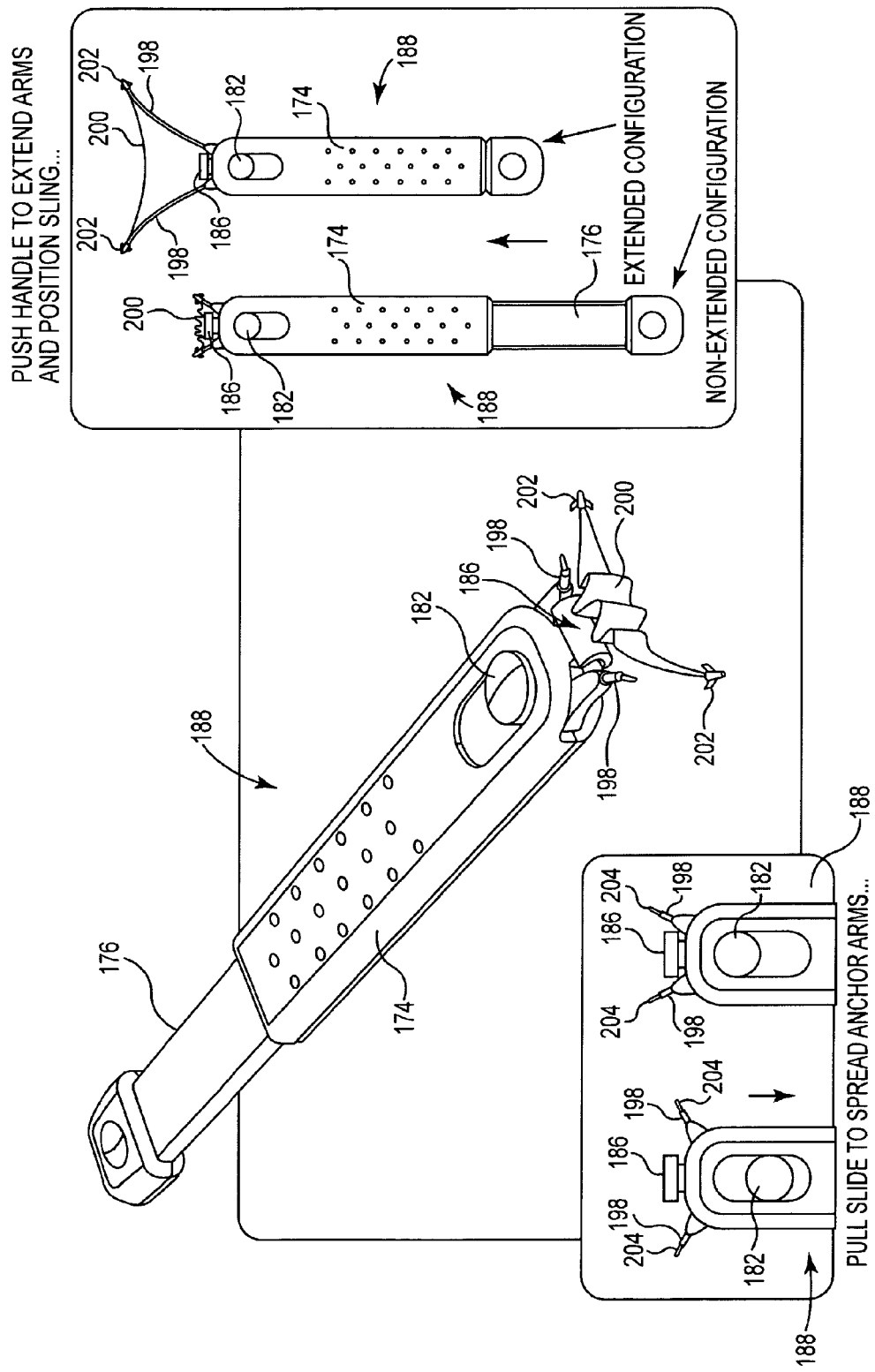
FIG. 11 illustrates an embodiment of a system as described, including a tool and an implant.

FIG. 11 illustrates a system for treating urinary incontinence, the system comprising a single-piece implant and a tool that includes two distal adjusting surfaces, each adjusting surface attached to a separate shaft that is moveable (extendable and retractable) relative to the tool. Tool 188 includes handle 174 and primary shaft 176. Handle 174 extends from a proximal end to surface 186 useful for contacting tissue. Two adjusting surfaces 204 are located at distal ends of moveable shafts 198. Each adjusting surface is capable of engaging a tissue fastener such as a self-fixating tip. Surface 186 extending laterally within space between shafts 198 is sized and shaped to contact and assist in approximating tissue of a urethra (e.g., corpus spongiosum, bulbospongiosus muscle, etc.). Shafts 198 are moveable (extendable and retractable) relative to handle 174 and surface 186, and are connected to primary shaft 176. Shafts 198 can be moved (extended and retracted relative to handle 174) by any mechanism, such as by movement of primary shaft 176 forward and back relative to handle 174. The angle or splay of shafts 198 (i.e., the angle of extended shafts relative to a longitudinal axis extending through the handle) can be adjusted by movement of angle adjustment 182.

Implant 200 as illustrated is a single-piece, e.g., integral mesh implant comprising a central tissue support portion, extension portions extending in opposite directions from the tissue support portion, and self-fixating tips 202.

In use, with primary shaft 176 extended proximally away from handle 174, and shafts 198 retracted into handle 174, implant 200 can be placed at the distal end of tool 188 with self-fixating tips 202 placed at each of two distal end adjusting surfaces 204. A user can grasp handle 174, and adjust the angle of the shafts 198 (relative to a longitudinal axis of the tool) by movement of angle adjustment 182. This may be referred to as a "non-extended" configuration (shafts 198 are non-extended). The distal end of tool 188, engaged with implant 200, can be inserted through the medial incision, whereupon surface 186 (also in contact with implant 200) can contact tissue of a region of a urethra to push or otherwise contact or place pressure on the urethra, to assist in approximating the urethra. Shafts 198 can then be extended (simultaneously) from handle 174 by movement of primary shaft 176 in a distal (toward the patient) direction while maintaining the position of handle 174 and surface 186. Self-fixating tips 202 become extended at distal ends of shafts 198 to contact and become secured to supportive tissue (e.g., in a region of an obturator foramen) in the pelvic region of the patient.

Figure 12:
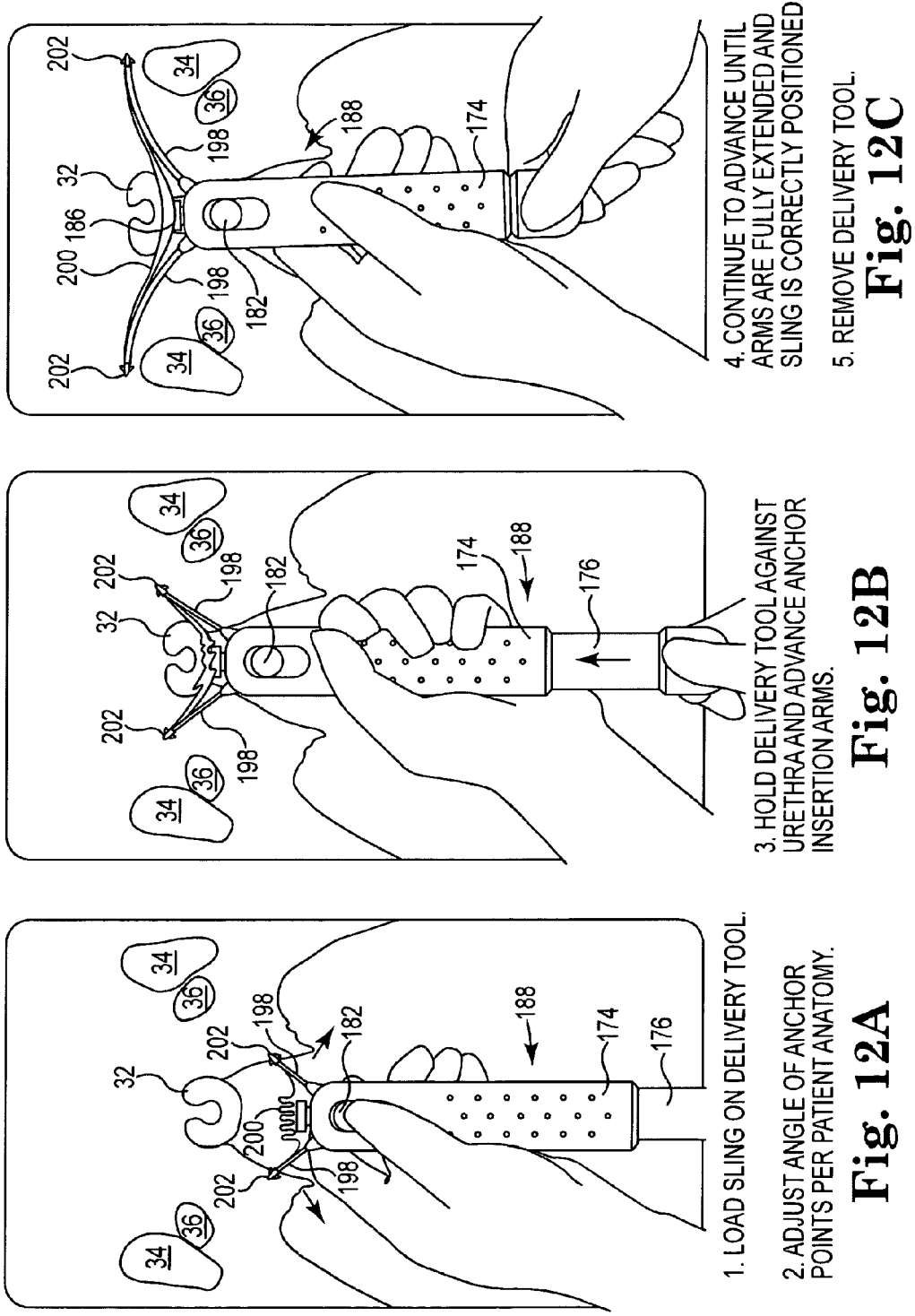
FIGS. 12A, 12B, and 12C illustrate an exemplary method useful with a described system.

FIGS. 12A, 12B, and 12C, illustrate a method of using tool 188 to place single-piece implant 200, to treat urinary incontinence. Patient anatomy is as described previously. Referring to FIG. 12A, with tool 188 in a non-extended configuration and implant 200 located at the distal end of tool 188, the distal end, including implant 200, is inserted through a medial incision in a patient to locate implant 200 at a location generally below a urethra. The angle of shafts 198 relative to a longitudinal axis of the tool can be adjusted (increased or decreased) by movement of angle adjustment 182. Surface 186 (also in contact with implant 200) can contact tissue of a region of a urethra to push or otherwise contact or place pressure on the urethra, to assist in approximating the urethra. Shafts 198 are extended (simultaneously) from handle 174 by movement of primary shaft 176 in a distal direction while maintaining the position of handle 174 and surface 186. Self-fixating tips 202 become extended at distal ends of shafts 198, to contact and become secured to supportive tissue in the pelvic region of the patient.

Figure 13:
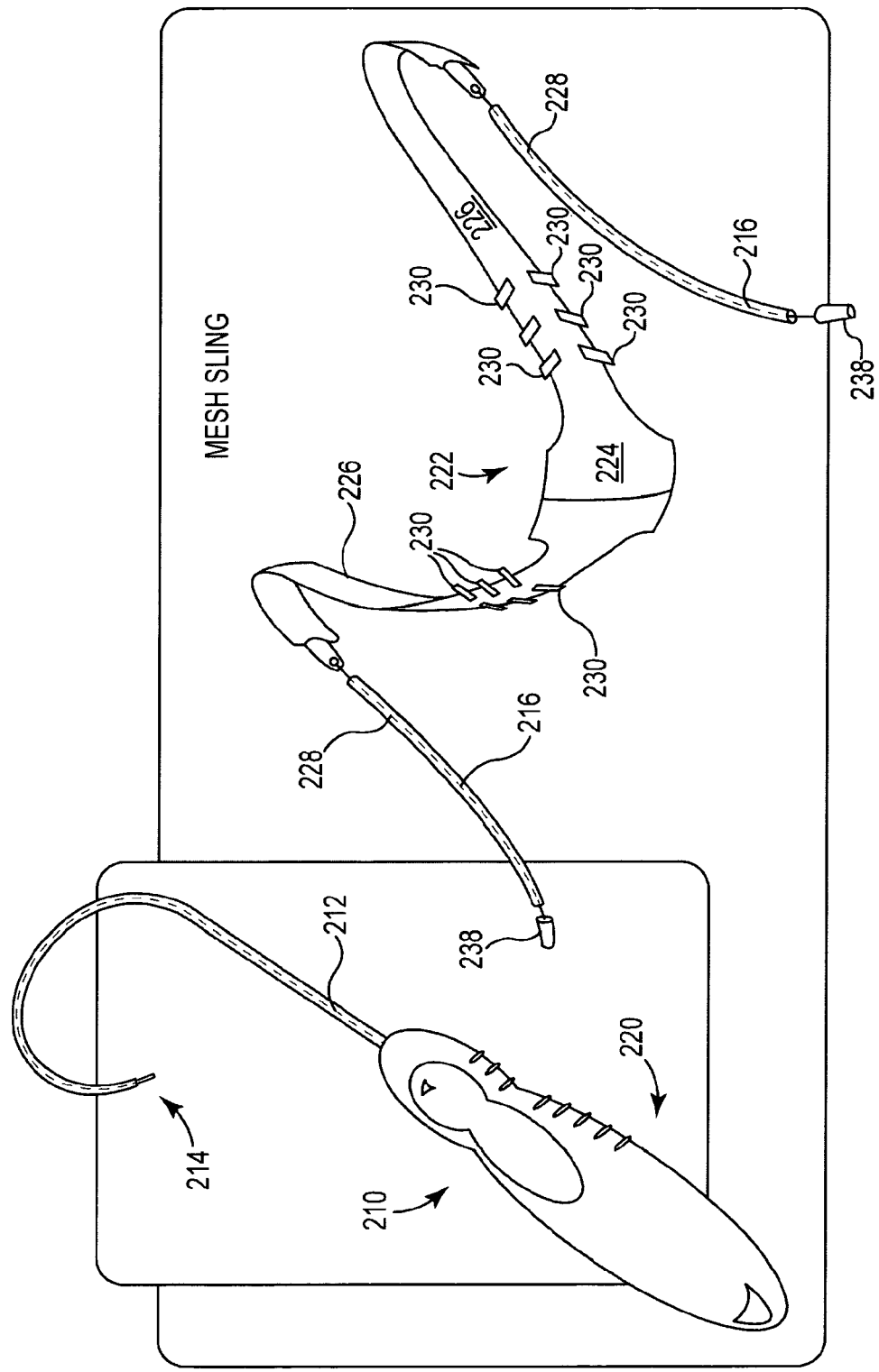
FIG. 13 illustrates an embodiment of a system as described, including a tool and an implant.

FIG. 13 illustrates a system that includes implant 222 (e.g., for treating male or female urinary incontinence) and one or more insertion tool 210. Implant 222 includes support portion 224, end or extension portions 226, tissue fasteners (chevrons or barbs) 230 located on extension portions 226 near support portion 224, tail portions (e.g., sutures) 216 extending from a distal end of each extension portion 226, connectors or dilators 238, and sheaths 228 which can be located along the lengths of extension portions 226 to cover tissue fasteners 230 (see FIG. 14A) (as illustrated at FIG. 13 sheaths 228 are located over tail portions 216). Insertion tool 210 includes shaft 212, distal end 214, proximal end and handle 220, and an optional mechanical release mechanism (e.g., detent) and trigger located at a proximal region of shaft 12 (optional release mechanism and trigger are not shown). FIG. 13 shows a single tool 210, having a helical shaft; optionally a system may include two tools 210 each having a helical shaft, one helical shaft suited to place an extension portion at a right side of a patient and one helical shaft suited to place an extension portion at a left side of the patient.

FIGS. 14A, 14B, and 14C, illustrate a method of using helically-curved tool 210 to place implant 222 to treat urinary incontinence. Patient anatomy is as described previously. On a first side of a patient, distal end of helical insertion tool 210, engaged with connector 238, is used to insert connector 238 through a medial incision, through an obturator foramen and related tissue, around a pubic ramus bone (34) and then subcutaneously back to the medial, midline perineal region. See FIG. 2A. Insertion tool 210 is then withdrawn and used to place the second connector 238 at a second side of the patient in a similar manner. See FIG. 14B. The implant can be adjusted and tensioned by adjusting the position of the implant and the urethra, including adjusting the position and tension of tail portions 216, which extend back to an external location through the medial incision. Once the urethra and implant are positioned as desired, sheaths 228 can be removed to expose extension portions 226, including tissue fasteners (anchors, barbs, or chevrons) 230 within tissue. See FIG. 14C.

Figure 15:
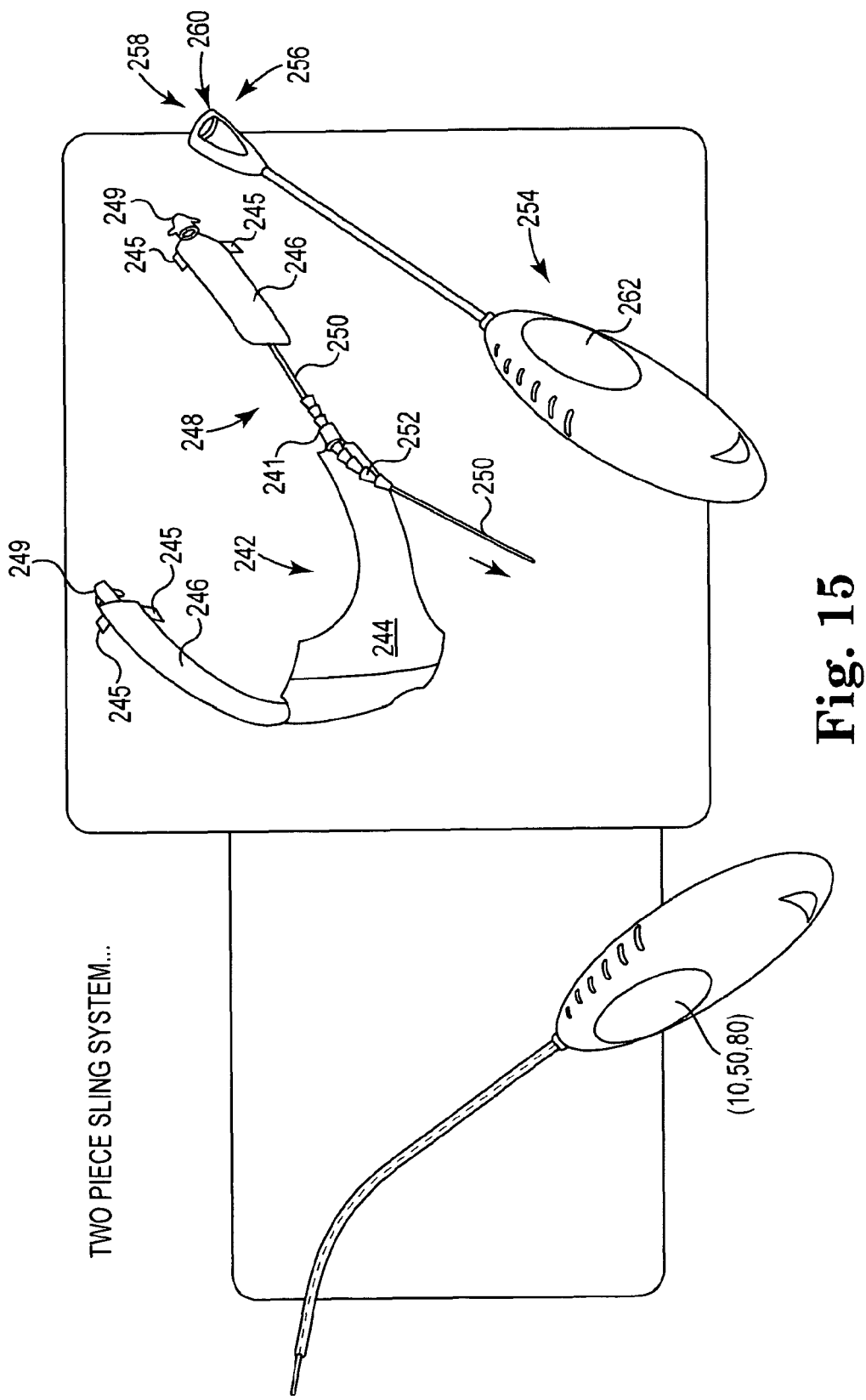
FIG. 15 illustrates an embodiment of a system as described, including a tool and an implant.

FIG. 15 illustrates a system that includes two-piece implant 242 (e.g., for treating male or female urinary incontinence), insertion tool (e.g., 10, 50, or 80), and adjusting (pusher) tool 254. Implant 242 includes a first piece that includes support portion 244, one extension portion 246 integrally connected to support portion 244, self-fixating tip 249, tissue anchors (chevrons or barbs) 245, and an aperture component 241 (e.g., grommet, channel, optionally comprising a one-way ratchet configuration) of an adjusting engagement, the aperture component 241 designed to engage a second component of the adjusting engagement. Extension portion piece 248 includes mesh portion 246, self-fixating tip 249, tissue anchors (chevrons or barbs) 245, and non-mesh portion 250, which includes a second component of an adjusting mechanism in the form of ratcheting "cones," teeth, or another form of ratchet surface, 252. Optionally (but not as illustrated) support portion 244 can be moveable along the length of the implant between self-fixating tips 249. Optionally an adjusting tool 254 can be used to engage aperture component 241 to assist in adjusting the adjusting engagement between aperture component 241 and ratchet surface 252. A proximal end of non-mesh portions 250 can be threaded through aperture 258 at distal end 256 of tool 254, and distal surface 260, surrounding aperture 258, can contact aperture component 241 to place pressure on aperture component 241 while non-mesh portion 252 is drawn in a proximal direction (see arrow).

Figure 16C:
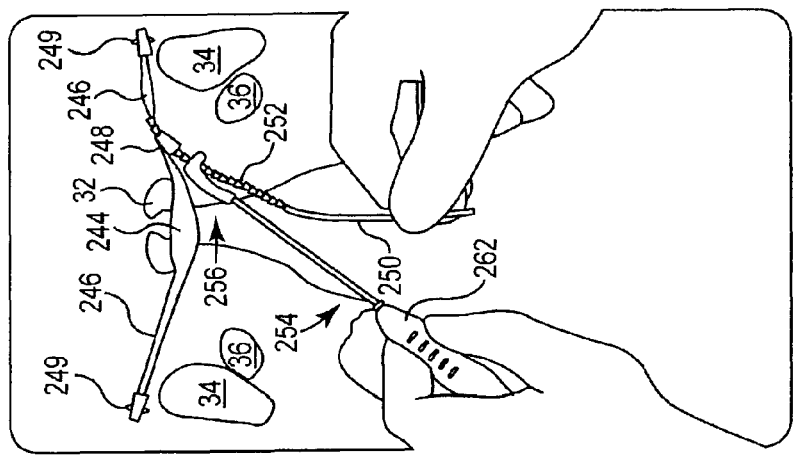
FIGS. 16A, 16B, and 16C illustrate an exemplary method useful with a described system.
Figure 16B:
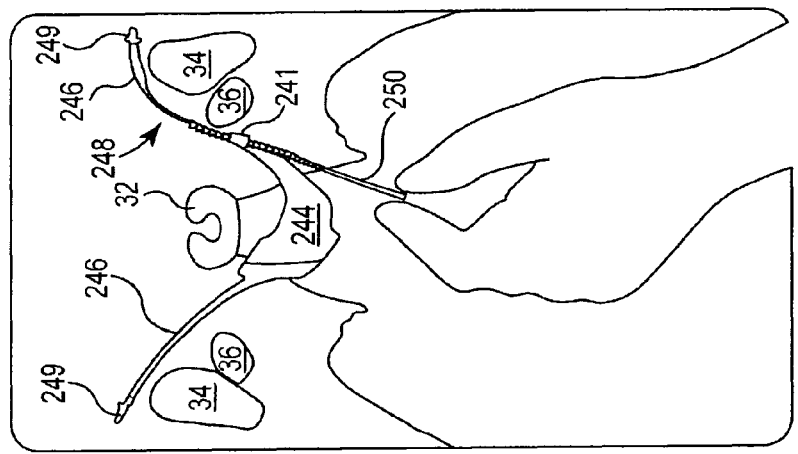
Figure 16A:
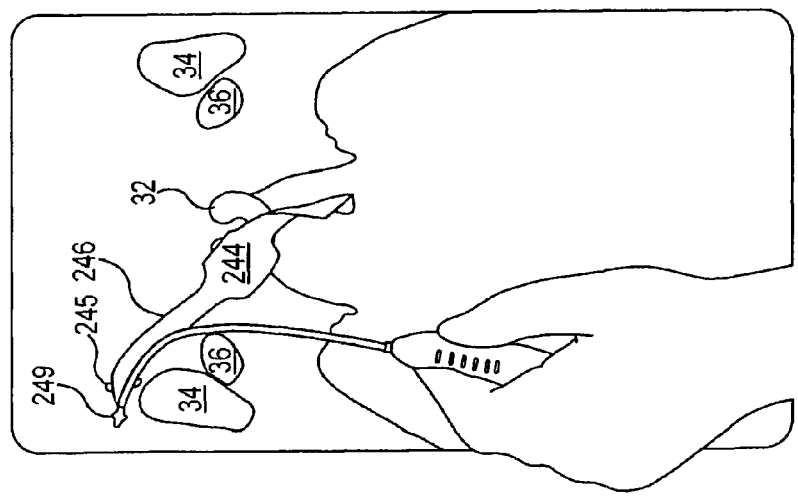

FIGS. 16A, 16B, and 16C, illustrate a method of using an insertion tool (e.g., 10) and adjusting tool 254 to place two-piece implant 242 to treat urinary incontinence. Patient anatomy is as described previously. A distal end of an insertion tool engaged with self-fixating tip 249 is used to insert self-fixating tip 249 through a medial incision and place self-fixating tip 249 at supportive tissue in a region of an obturator foramen on a first side of the patient. See FIG. 16A. The insertion tool is then used to engage the second self-fixating tip 249, and the second self-fixating tip 249 can be placed at supportive tissue in a region of an obturator foramen on a second side of the patient. A proximal end of non-mesh portion 250 can be placed through an aperture of aperture component 241 and pulled to adjust a length of implant between self-fixating tips 249, to provide desired tension on the length of implant, and desired approximation, placement, and support of the urethra. See FIGS. 16B and 16C. Proximal end 250 may optionally be threaded through aperture 258 of pusher tool 254, and pusher tool 254 may optionally be used to push aperture component 241 in a distal direction, toward self-fixating tip 249 located at the distal end of mesh portion 246 of extension portion piece 248. A proximal portion of non-mesh portion 250 can then be removed by cutting. Before, after, or simultaneously with reducing the length of implant by pulling non-mesh portion 250 relative to aperture component 241, an optional moveable support portion (not shown) can be moved (slid) laterally in a direction toward one or the other obturator foramen to place the moveable support portion at a desired (central, medial) location below the urethra.

Figure 17A:
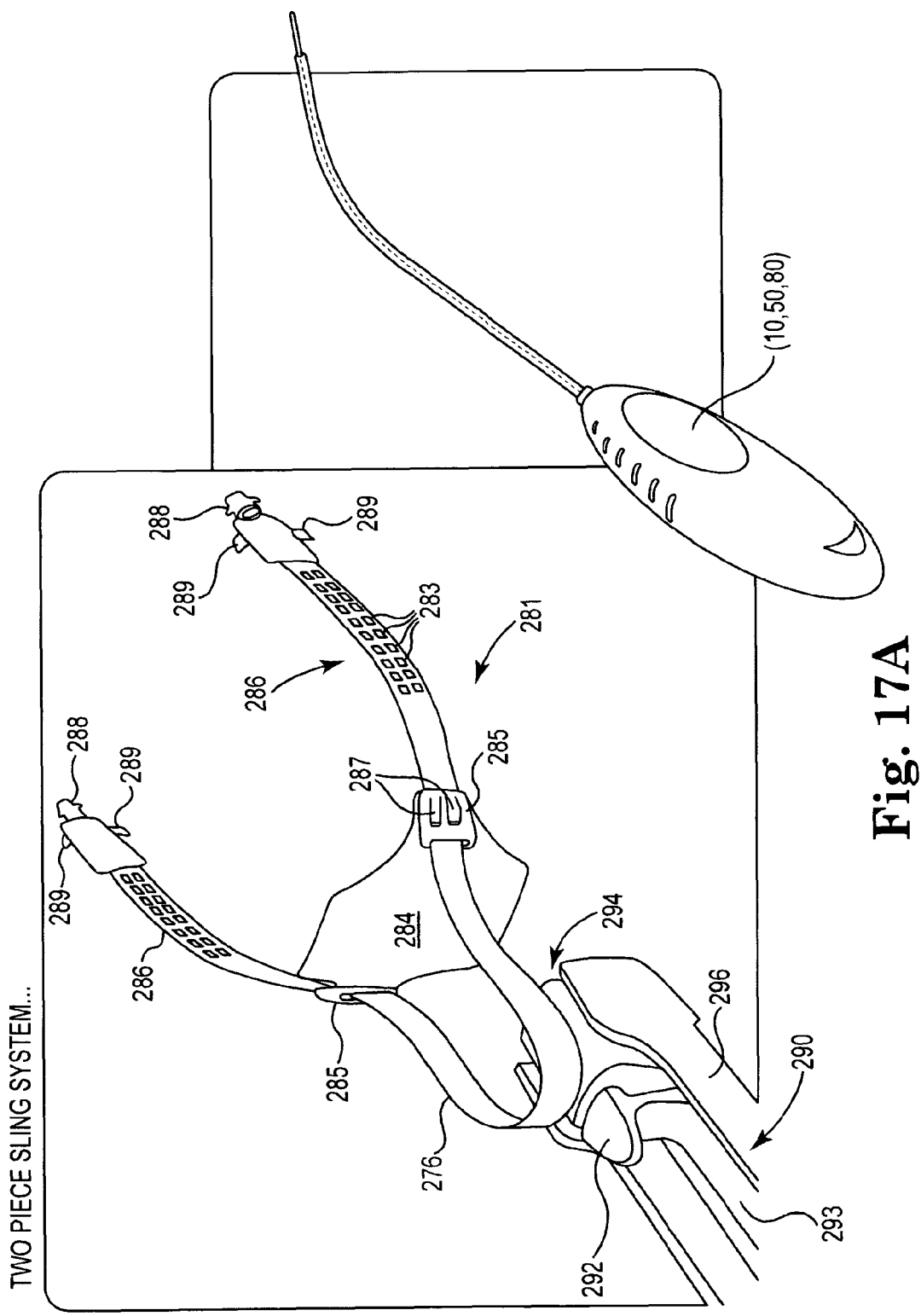
FIGS. 17A and 17B illustrate embodiments of systems as described, including tools and an implant.

FIG. 17A illustrates a system that includes implant 281 (e.g., for treating male or female urinary incontinence) and insertion tool 290. Implant 281 includes support portion 284, end or extension portions 286, self-fixating tips 288, and tissue fasteners (chevrons, barbs) 289. Support portion 284 is moveable relative to self-fixating tips 288 by passage through supports 285 located on support portion 284. Supports 285 are adjusting engagements that allow support portion 284 to be moved and positioned at a desired location along a length of each extension portion 286. The effect is to allow a user to reduce (or optionally increase) the effective size of each extension portion by sliding each support 285 toward a respective self-fixating tip 288, on one or both sides of the implant and patient, thereby reducing the overall length of implant 281 between self-fixating tips 288. As illustrated, supports 285 include ratcheting springs 287, which are biased toward and contact perforations 283 of extension portions 286, resulting in a one-way adjusting engagement between a support 285 and a perforated extension portion 286.

Figure 17B:
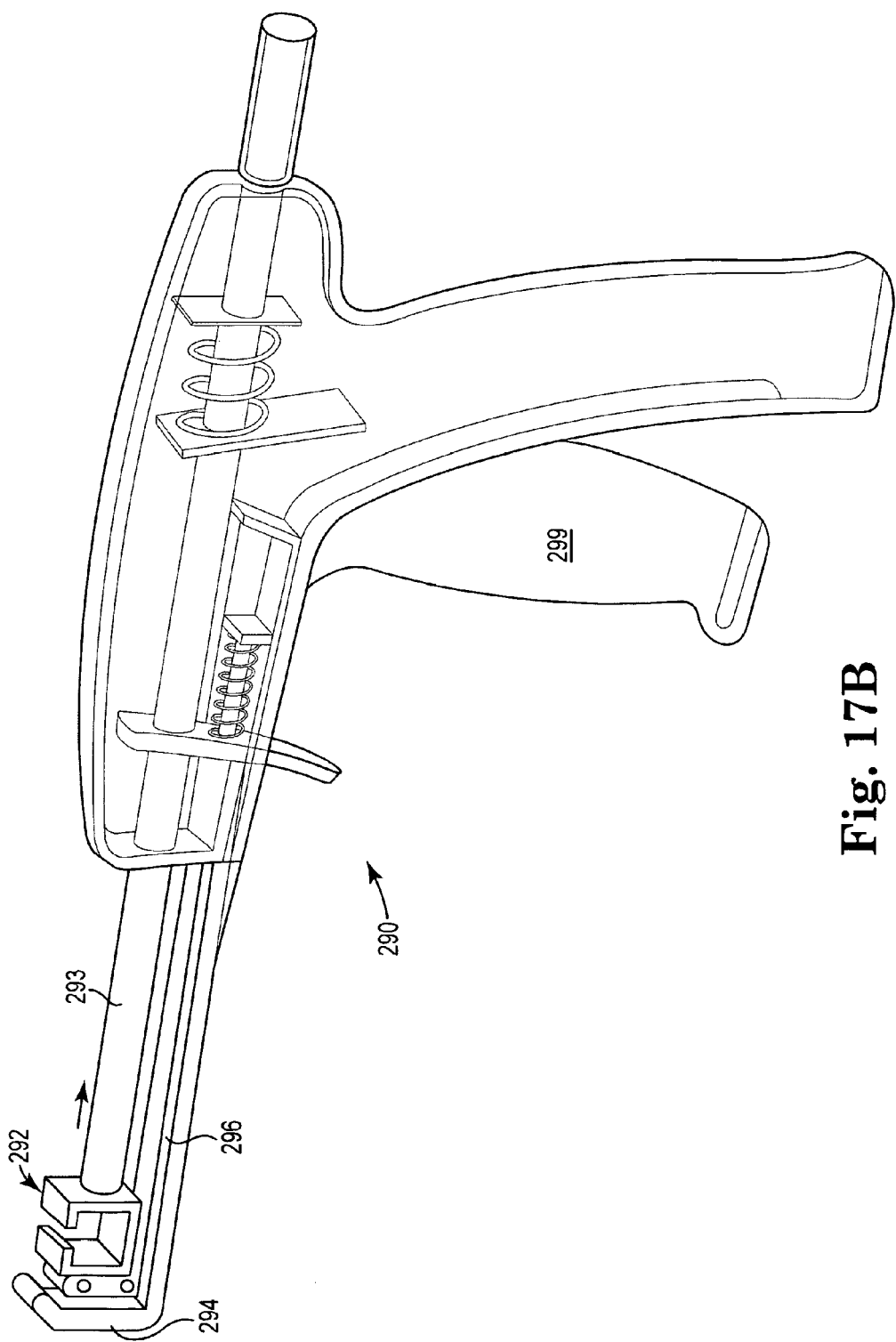

FIG. 17B shows details of an exemplary tool 290, wherein handle 299 is moved proximally (away from the patient) to draw shaft 293 in the proximal direction. Tool 290 can also optionally include a gauge to measure a state of adjustment of the implant during placement and adjustment, including tension in the implant during adjustment. For example, a gauge may measure the amount of tension applied to the extension portions of the implant by use of a pressure gauge that measures pressure at surface 292. Alternately, a gauge may be used to measure pressure of tissue (e.g., corpus spongiosum) that becomes applied to a distal end of the tool, e.g., at surface 294.

In use, after placement of self-fixating tips at a left and a right side of a patient, tool 290 can be used to moved supports 285 distally along support portions 286, toward self-fixating tips 288, to shorten the length of implant between self-fixating tips 288. Movement of supports 285 can be assisted by use of tool 290, which includes distal surface 294 at an end of stationary shaft 296. Surface 294 is capable of contacting and approximating support portion 284, placed in contact with tissue of a urethra (e.g., corpus spongiosum, bulbospongiosus muscle). Puller 292 is located behind surface 294 and at a distal end of moveable shaft 293. To adjust lengths of extension portions 286, proximal loop 276 is placed on a proximal side of puller 292, as surface 294 is placed against support portion 284, in contact with tissue of a urethra, and after self-fixating tips are placed in supportive tissue. Moveable shaft 293 is advanced in a proximal direction (see arrows), causing support portion 284 to move distally along lengths of extension portions 286 and toward self-fixating tips 288; i.e., proximal portions of extension portions 286 are pulled in a proximal direction through supports 285. The result is to shorten the length of implant between self-fixating tips 288, while approximating the urethra, and thereafter supporting the urethra with implant 281.

Figure 18C:
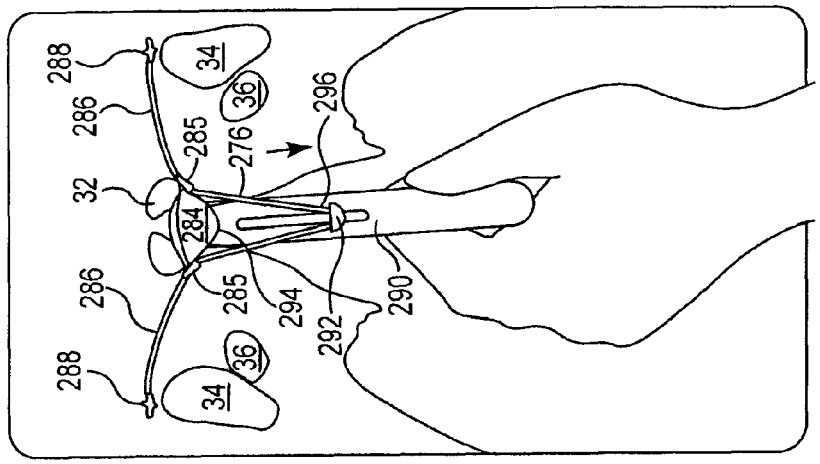
FIGS. 18A, 18B, and 18C illustrate an exemplary method useful with a described system.
Figure 18B:
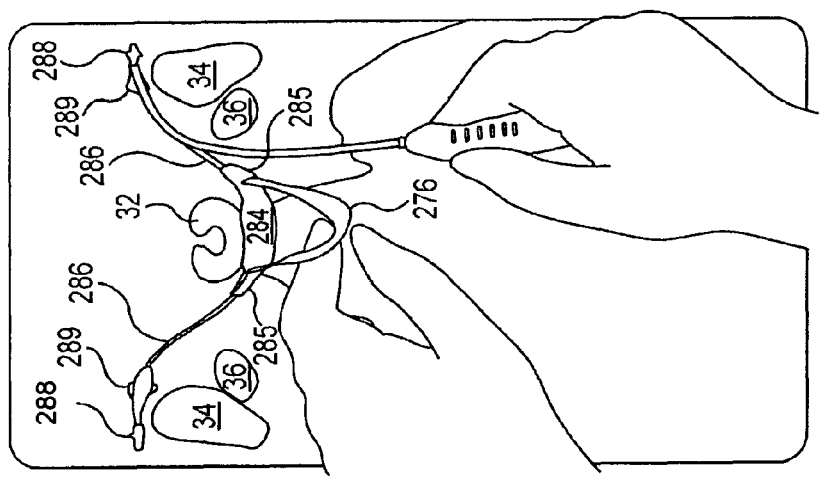
Figure 18A:
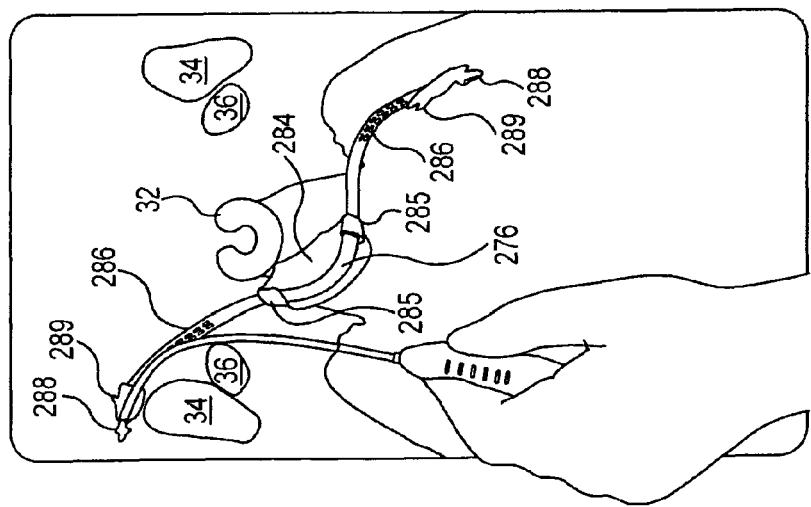

FIGS. 18A, 18B, and 18C, illustrate a method of using an insertion tool (e.g., 10, 50, or 80) and adjusting tool 290 to place implant 281 to treat urinary incontinence. Patient anatomy is as described previously. A distal end of an insertion tool is used to place self-fixating tips 288 at a region of an obturator foramen on a first side and a second side of the patient. See FIGS. 18A and 18B. Adjusting tool 290 is then used to adjust the placement of the implant and the location of the urethra. For example, proximal loop 276 can be placed on a proximal side of puller 292 as surface 294 is placed against support portion 284 and in contact with tissue of a urethra. Tool 290 can be used to approximate tissue of the urethra as desired. Moveable shaft 293 is advanced in a proximal direction causing support portion 284 to move distally along the lengths of extension portions 286 and toward self-fixating tips 288; i.e., proximal portions of extension portions 286 are pulled in a proximal direction through supports 285. The result is to shorten the length of implant between self-fixating tips 288 while approximating the urethra, and thereafter supporting the urethra with implant 281. Tool 290 can be removed and proximal loop 276 can be cut away.

Figure 19:
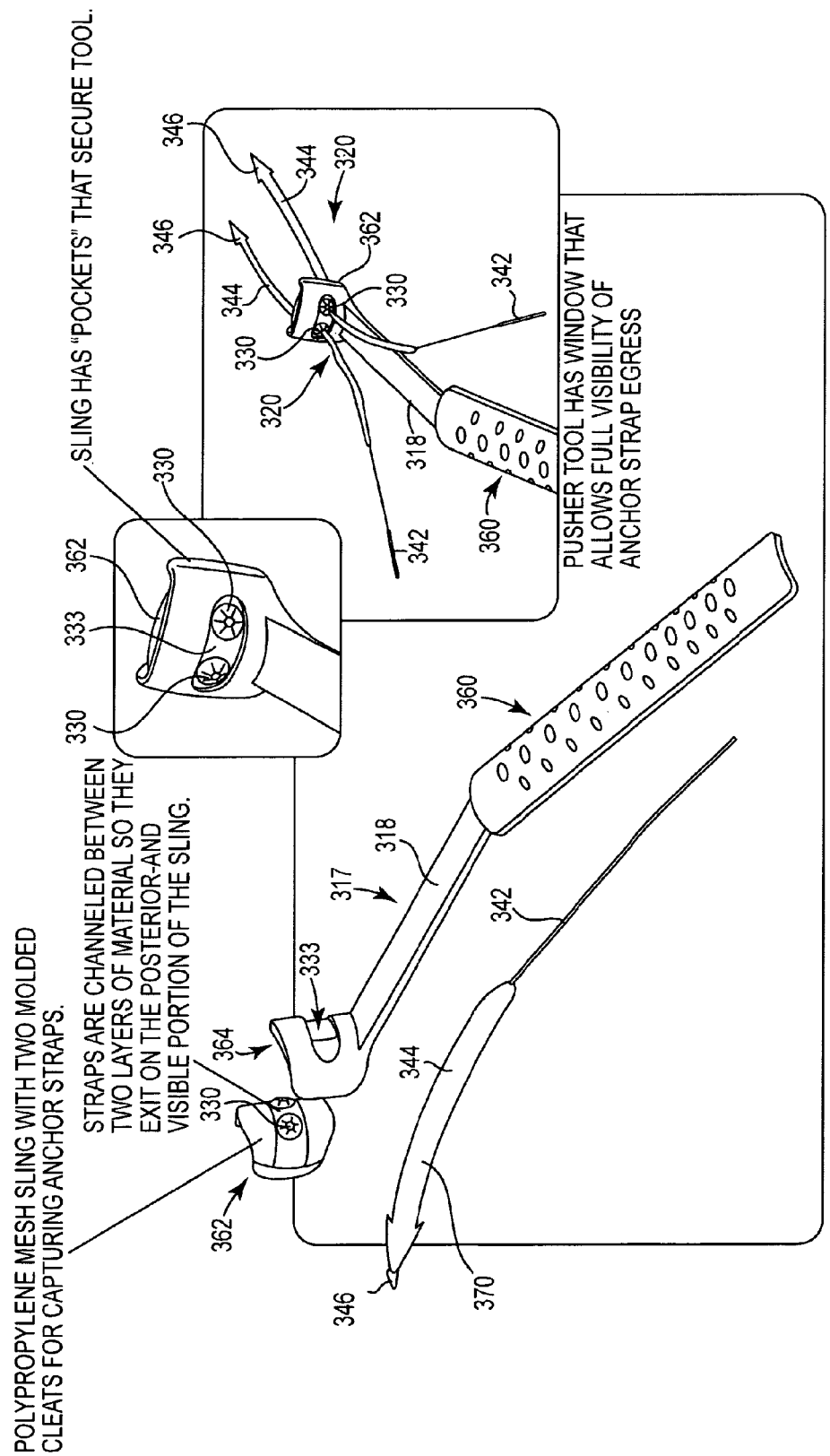
FIG. 19 illustrates an embodiment of a system as described, including a tool and an implant.

FIG. 19 illustrates a system for treating urinary incontinence, the system comprising a multi-piece implant and an adjusting tool. The system shares structural features with the systems illustrated elsewhere herein, including the systems of FIGS. 7 and 9, and can be used in methods as described for those systems to place an implant into a patient using steps analogous to steps identified as useful with those systems. Adjusting tool 317 includes handle 360 and distal adjusting surface 364, in contact with support portion piece 362. Shaft 318 extends from a proximal shaft end at handle 360 to surface 364 defined adjacent to aperture 333. The curved distal surface 364 adjacent to aperture 333 is sized and shaped to contact and assist in approximating tissue of a urethra (e.g., corpus spongiosum, bulbospongiosus muscle, etc.) during use of tool 317 to place an implant to support the urethra.

A multi-piece implant includes support portion piece 362 and two extension portion pieces 370. Extension portion pieces 370 include a mesh portion 344, a non-mesh portion 342, and self-fixating tip 346. Support portion piece 326 includes a surface to support a urethra having two apertures 330; each aperture 330 can be a component of an adjusting engagement with non-mesh portion 342 or mesh portion 344. Non-mesh portions 342 include a surface or structure that can frictionally engage an aperture 330 to provide an adjusting engagement between aperture 330 and non-mesh portion 342, the adjusting engagement being, e.g., a one-way or a two-way adjusting engagement. As illustrated, non-mesh portion 312 includes a polymeric rod that has surfaces that engage a one-way frictional structure (e.g., grommet) at each aperture 330.

In use, after placing each extension portion piece at a desired patient location, e.g., as described herein with self-fixating tips at supportive tissue, support portion piece 326 can be placed at distal surface 364 of tool 317 with apertures 330 seated to be accessed through aperture 333. Proximal ends of extension portion pieces 370 can be passed through aperture 330 and aperture 333. A user can grasp (by hand or by use of a tool) a proximal end of each support portion piece 370 to pull the proximal end in a proximal direction. Simultaneously, surface 364 can be used to approximate tissue of a urethra by inserting the distal end of tool 317 through a medial incision to contact tissue of a region of a urethra, to push or otherwise contact or place pressure on the urethra, to assist in approximating the urethra. The extension portion pieces can be drawn through apertures 330 to adjust the length of the extension portions and the location of the tissue support portion.

Figure 20:
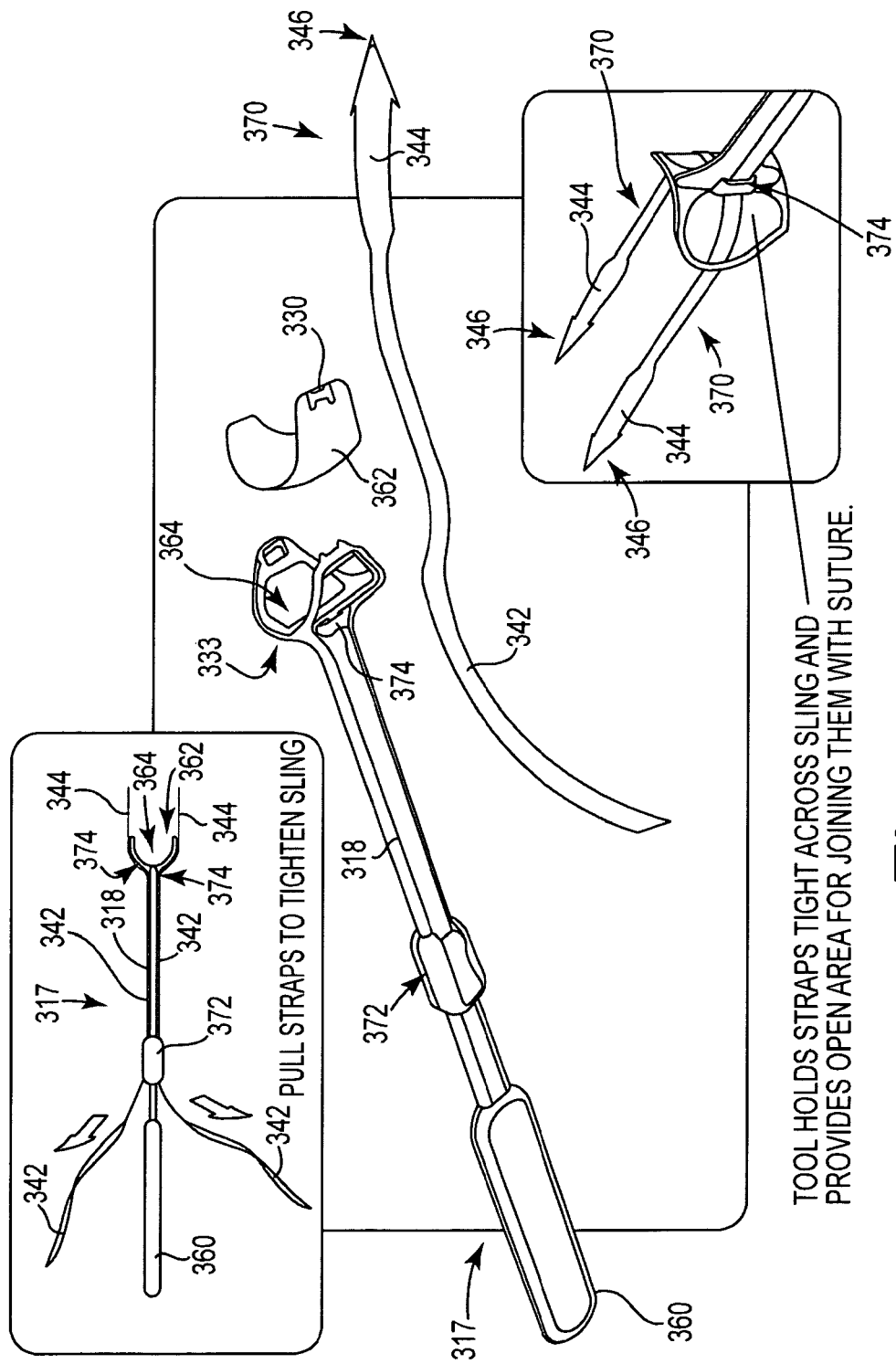
FIG. 20 illustrates an embodiment of a system as described, including a tool and an implant.

FIG. 20 illustrates a system for treating urinary incontinence, the system comprising a multi-piece implant and an adjusting tool. The system shares structural features with the systems illustrated elsewhere herein, including the systems of FIGS. 7, 9, and 19, and can be used in methods as described for those systems to place an implant into a patient using steps analogous to steps identified as useful for those systems. Compared to the system of FIG. 19, the system of FIG. 20 includes similar features that include adjusting tool 317, handle 360, distal adjusting surface 364, support portion piece 362, extension portion pieces 370, shaft 318, and surface 364 defined adjacent to aperture 333. As one difference, extension portion piece 370 of FIG. 20 includes a proximal portion made of mesh (as a replacement for the non-mesh portion). Also, tool 317 includes moveable holder (e.g., slider or "shuttle") 372 moveable along a length of shaft 318, and guides 374 located at a distal end of shaft 318, near surface 364. During use, proximal mesh portion 342 is guided through aperture 330 of support portion piece 362, through guide 374 at a distal end of shaft 318, and then can removably engage slider 372 by a removable mechanical connection such as a cleat, slot, slit, moveable jaws, a moveable frictional device, or any mechanical securing device. Slider 372 can be moved in a proximal direction to pull extension portion pieces in a proximal direction (toward handle 360 along shaft 318) relative to support portion 362 located against surface 365, while the distal end of tool 317 is used to approximate urethral tissue.

Figure 21:
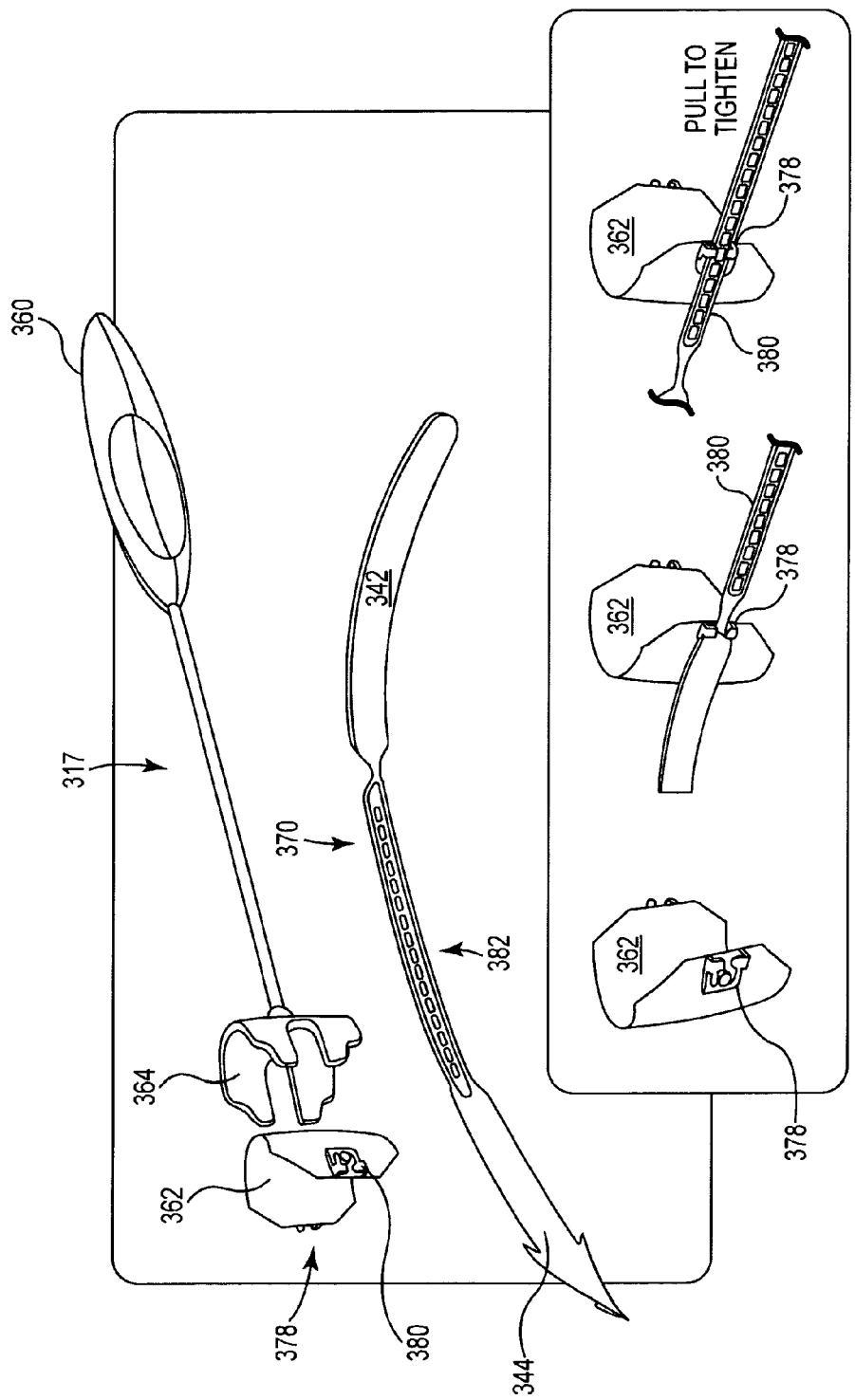
FIG. 21 illustrates an embodiment of a system as described, including a tool and an implant.

FIG. 21 illustrates a system for treating urinary incontinence, the system comprising a multi-piece implant and an adjusting tool. The system shares structural features with the systems illustrated elsewhere herein, including the systems of FIGS. 7, 9, 19, and 20, and can be used in methods as described as useful with those systems. Compared to the system of FIGS. 19 and 20, the system of FIG. 21 includes similar features, identified numerically in a consistent manner. As one difference, extension portion piece 370 of FIG. 21 includes a non-mesh portion 380 that includes apertures. Non-mesh portion 380 can be threaded through buckle 378 of support portion piece 326 to allow apertures of the non-mesh portion to selectively engage and disengaged buckle 378. The adjusting engagement between support portion piece 362 and extension portion pieces 370 is capable of being engaged, disengaged, adjusted, re-engaged, and disengaged, adjusted, and re-engaged as necessary. The adjusting engagement is a two-way engagement that can be selectively secured (e.g., "locked into place"), unsecured, and re-secured. Each support portion piece 370 can be used as described, by engaging supportive tissue, then threading support portion pieces 370 through buckles 378. Each support portion piece 370 can then be individually engaged (through an aperture 380) with buckle 378 and the implant can be tested for positioning, tension, or support of the urethra. If desired, each support portion piece can be independently disengaged from buckle 378, adjusted, then re-engaged. Upon proper placement, support, tension, etc., a proximal portion of each support portion piece can be trimmed.

Figure 22:
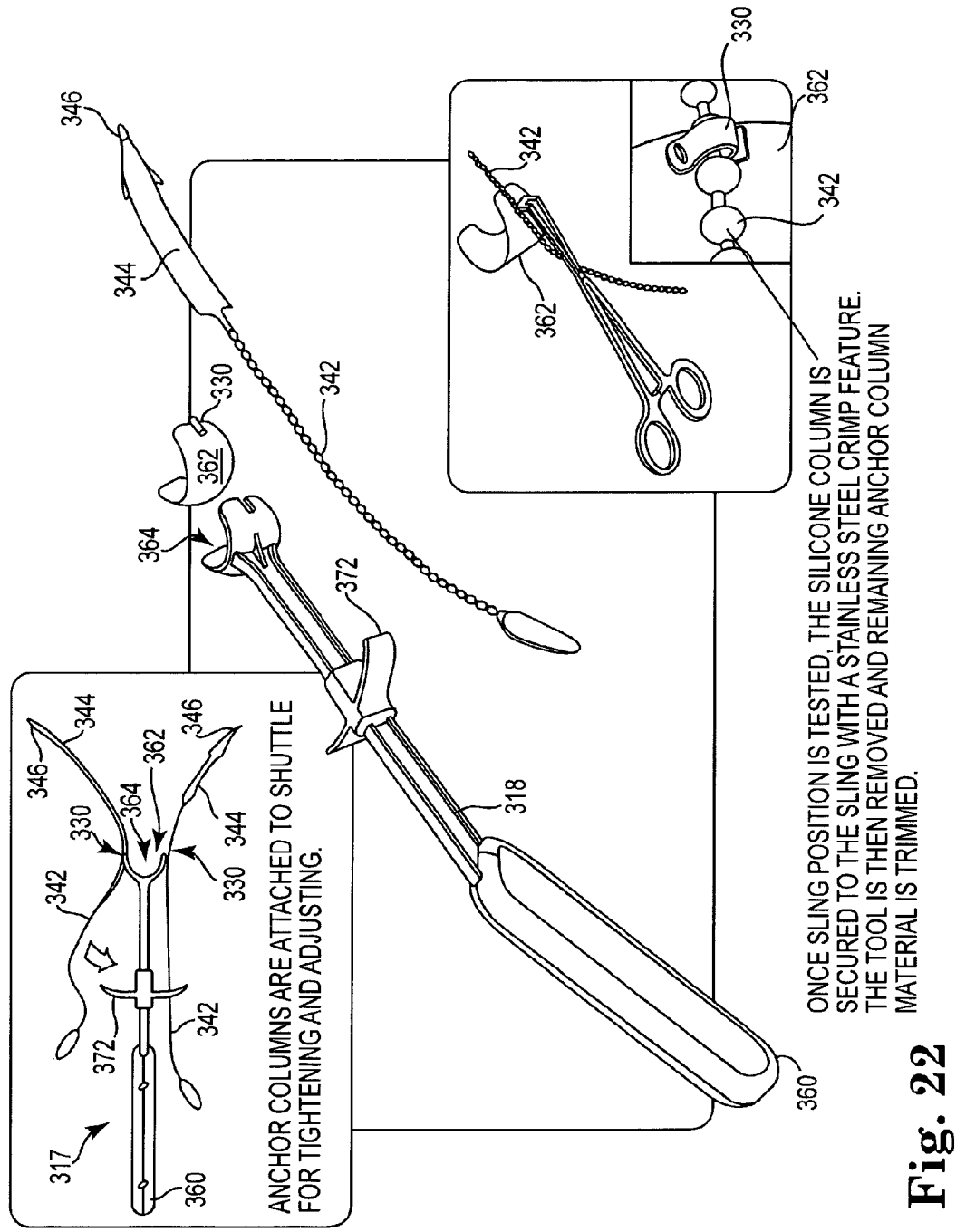
FIG. 22 illustrates an embodiment of a system as described, including a tool and an implant.

FIG. 22 illustrates another system for treating urinary incontinence, the system comprising a multi-piece implant and an adjusting tool. The system shares structural features with systems illustrated elsewhere herein, including the systems of FIGS. 7, 9, 19, 20, and 21, and can be used in methods described as useful for those systems. Compared to the system of FIG. 20, the system of FIG. 22 includes similar features that include adjusting tool 317, handle 360, distal adjusting surface 364, support portion piece 362, extension portion pieces 370, shaft 318, slider or "shuttle" 372, and surface 364 defined adjacent to aperture 333. As a difference, aperture piece 330 (e.g., of a metal such as stainless steel) is a two-way adjusting engagement that can be closed or locked (e.g., mechanically crimped) to prevent subsequent movement of non-mesh portion 342 after adjustment of extension portion piece 370.

According to certain preferred methods of treating incontinence in a male, using implants as described, an implant can be placed below a urethra to contact tissue of a corpus spongiosum (by dissecting bulbospongiosus muscle), and the urethra can be approximated to improve continence without requiring the urethra to be compressed.

As described more specifically in US 2006-0287571-A1, according to exemplary embodiments of treating incontinence using any of the implants or tools described herein, a tissue support portion of an implant can be placed in a position to approximate and support a urethra, optionally without placing compressive forces on the urethra, to effect improved continence (e.g., in a male patient). Preferably, for treatment of a male patient, a tissue support portion can be placed to contact tissue of a corpus spongiosum and then tensioned to cause approximation of the corpus spongiosum and urethra in a direction toward a bladder, optionally with use of a tool as described herein for placing pressure on or moving the urethra. Accordingly, embodiments of the invention generally, in a male patient, can relate to placement of a tissue support portion at a location that supports and is tensioned to reposition a urethra toward a bladder. The implant can be tensioned to cause the urethra—especially the posterior portion of urethra above a perineal membrane—to be moved from an abnormal (e.g., prolapsed or descended) position to a position of normal healthy urethral tissue capable of being fully coated upon contraction of the rhabdosphincter. Alternate methods can cause compression of the urethra, but compression is not required in methods that result in approximation of the urethra to improve continence.

According to these embodiments, a method of surgically installing a urethral implant can include providing a medial incision at the perineum of a male patient to expose bulbospongiosus muscle, optionally and preferably dissecting through bulbospongiosus muscle to expose corpus spongiosum, and placing a tissue support portion of the implant to contact the corpus spongiosum tissue. Optionally the tissue support portion can be fixed to the corpus spongiosum, such as by use of a medical attachment in the form of a suture, staple, adhesive, or the like. The implant can be adjusted, tensioned, etc., e.g. based on the use of an adjusting engagement, an adjustment tool, or another means, to approximate the urethra to improve continence, and tension can optionally and preferably maintained chronically.

According to exemplary methods, the implant can be inserted through a single medial (perineal or vaginal) incision (no external incision is required) and an extension portion of the implant can be attached to supportive tissue within the pelvic region, such as tissue at a region of an obturator foramen, or to tissue (e.g., fascia) that lies between a urethra and tissue of an obturator foramen, or other supportive tissue. According to such methods, a tissue fastener such as a self-fixating tip at a distal end or distal portion of an extension portion can be engaged at a distal end of an insertion tool (e.g. a curved elongate needle). The insertion tool can be used to place the tissue fastener and extension portion through a medial incision (of a male or female patient) and extend the tissue fastener and extension portion in a direction of an obturator foramen, e.g., to tissue of the obturator foramen or to other supportive tissue. Features of the inventive methods, implants, and tools that are described herein can be incorporated into such a technique, such as placement of the urethral sling below a urethra at a tissue of a bulbospongiosus muscle or a corpus spongiosum, approximation of the urethra to improve continence (without the need for compression of the urethra), etc., use of an implant that includes adjustable engagements (and steps of adjusting the implant), use of an adjustment tool. This method avoids the need for lateral incisions at the inner thigh and adjacent to each opposing obturator foramen.

The invention claimed is:

1. A system for treating urinary incontinence, the system comprising a multi-piece implant comprising a support portion piece and an extension portion piece, and an adjusting tool, wherein
    the support portion piece comprises a tissue support portion sized and shaped for placement to support a urethra, and
    the extension portion piece comprises a proximal end, a distal end, an extension portion extending between the proximal end and the distal end, and a tissue fastener, and is adjustably connectable to the support portion piece at an adjusting engagement, and
    the adjusting tool comprises
        a surface at a distal end of a shaft capable of engaging the support portion piece, and
        a holder attached to the shaft and capable of holding the proximal end of the extension portion piece and moving the proximal end by pulling the proximal end relative to the surface, in a proximal direction, while the support portion piece is engaged with the surface.

2. A system according to claim 1 wherein the surface is adjacent to an opening.

3. A system according to claim 1 wherein the adjusting tool comprises the shaft and a yoke, the surface is located at the yoke, the yoke is stationary relative to the shaft, and the moveable holder is moveable relative to the shaft.

4. A system according to claim 1 wherein the adjusting tool comprises a gauge to measure tension of the implant during placement of the implant in a patient.

5. A system according to claim 1 wherein the adjusting engagement comprises an aperture through which the extension portion piece extends to adjustably connect the extension portion piece to the support portion piece.

6. A system according to claim 1 wherein the adjusting engagement is selected from: a one-way adjusting engagement, a two-way adjusting engagement, and a locking two-way adjusting engagement.

7. A system according to claim 1 wherein the implant comprises
    a second extension portion piece comprises a proximal end, a distal end, a second extension portion extending between the proximal end and the distal end, and a tissue fastener, and is adjustably connectable to the support portion piece at an adjusting engagement, and
    supportive portions consisting of the tissue support portion, the extension portion, and the second extension portion.

8. A method of treating urinary incontinence, the method comprising:
    providing the system according to claim 7,
    creating a medial incision in the patient,
    dissecting from the medial incision to tissue below a urethra,
    placing the support portion piece to contact tissue to support the urethra,
    placing a distal end of the first extension portion in a tissue path extending toward a first obturator foramen of the patient, and
    placing a distal end of the second extension portion in a tissue path extending toward a second obturator foramen of the patient.

9. A system according to claim 7 wherein the extension portion piece is disconnected from the support portion piece, and wherein the second extension portion piece is disconnected from the support portion piece.

10. A system according to claim 9 wherein the adjusting tool comprises a second holder attached to the shaft and capable of holding the proximal end of the second extension portion piece and moving the proximal end of the second extension portion piece by pulling the proximal end of the second extension portion piece relative to the surface, in a proximal direction, while the support portion piece is engaged with the surface.

11. A method of treating urinary incontinence in a male or a female patient, the method comprising providing the system according to claim 1, placing the implant below a urethra of the patient, and placing the tissue fastener at supportive tissue.

12. A system according to claim 1 wherein the holder is slidably attached to the shaft.

13. A system according to claim 1 wherein the holder is slidably attached to the shaft through a rider, the rider being engaged with and capable of moving along a length of the shaft while remaining attached to the shaft and while the holder is holding the proximal end of the extension portion piece.

14. A system according to claim 1 wherein the holder is capable of holding the proximal end of the extension portion piece and moving the proximal end relative to the surface, while the holder remains attached to the shaft.

15. A system according to claim 1 wherein the extension portion piece is disconnected from the support portion piece.

16. A system for treating urinary incontinence, the system comprising an implant and a tool,
    the implant comprising
        a support portion, two extension portions, and two self-fixating tips, one self-fixating tip at an end of each extension portion, and
        at least one guide tube comprising a proximal end and a distal end attached to one of the two self-fixating tips, the distal end being capable of being removed from the one self-fixating tip,
    the tool comprising a handle and a shaft having a distal end capable of engaging the one self-fixating tip, and an optional release mechanism at the distal end, the optional release mechanism being capable of selectively engaging and releasing the one self-fixating tip,
    wherein the shaft distal end is capable of being inserted into the proximal end of the at least one guide tube and engaging the guide tube to allow the shaft distal end to be moved distally within the guide tube to become engaged with the at least one self-fixating tip while the guide tube is attached to the one self-fixating tip.

17. A system according to claim 16 wherein the shaft is capable of being inserted into the guide tube.

18. A system according to claim 17 comprising two guide tubes, each guide tube comprising a distal end removably engaged with one of the two self-fixating tips.

* * * * *